(12) United States Patent
Hsu et al.

(10) Patent No.: US 7,531,313 B2
(45) Date of Patent: May 12, 2009

(54) SCREENING FOR AGENTS THAT MODULATE RELAXIN FUNCTION

(75) Inventors: Sheau Yu Hsu, Menlo Park, CA (US); Aaron J. W. Hsueh, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/497,641

(22) Filed: Aug. 1, 2006

(65) Prior Publication Data

US 2007/0054297 A1 Mar. 8, 2007

Related U.S. Application Data

(62) Division of application No. 10/222,668, filed on Aug. 15, 2002, now abandoned.

(60) Provisional application No. 60/313,259, filed on Aug. 17, 2001.

(51) Int. Cl.
*G01N 33/53* (2006.01)
*C07K 14/705* (2006.01)
*C12N 5/10* (2006.01)

(52) U.S. Cl. .................. 435/7.1; 530/350; 435/325
(58) Field of Classification Search .................. None
See application file for complete search history.

(56) References Cited

U.S. PATENT DOCUMENTS

| 4,758,516 A | 7/1988 | Hudson et al. |
| 4,871,670 A | 10/1989 | Hudson et al. |

FOREIGN PATENT DOCUMENTS

| WO | WO 99/48921 A1 | 9/1999 |
| WO | WO-9948921 A1 * | 9/1999 |
| WO | WO 02/14489 A2 | 2/2002 |

OTHER PUBLICATIONS

Hsu et al. Activation of orphan receptors by the hormone relaxin. Science 295: 671-674, 2002.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Kohsaka, et al. (1998) *Biol. Reprod.*, 59(4):991-999.
Tan, et al. (1999) *Br. J. Pharmacol.*, 127(1):91-98.
Ivell (1997) *Rev. Reprod.*, 2:133-138.
Boockfor, et al. (2001) *Reproduction*, 122:899-906.
Smith, et al. (2001) *J. Pept. Sci.*, 7:495-501.
Overbeek, et al. (2001) *Genesis*, 30:26-35.
Hsu, et al. (2000) *Mol. Endocrinol.*, 14(8):1257-1271.
Adham, et al. (1993) *J. Biol. Chem.*, 268:26668-26672.
Ferlin, et al. (2003) *J. Clin. Endocrinol. & Metab,*, 88(9):4273-4279.
Kumagai, et al., (2002) *J. Biol. Chem.*, 277(35):31283-31286.
Genbank Accession No. AC098607, Muzny et al. Oct. 9, 2002.
Genbank Accession No. AC098990, Muzny et al. Oct 15, 2002.

* cited by examiner

*Primary Examiner*—Bridget E Bunner
(74) *Attorney, Agent, or Firm*—Bozicevic, Field & Francis LLP; Pamela J. Sherwood

(57) ABSTRACT

High affinity relaxin receptors, polypeptide compositions related thereto, as well as nucleotide compositions encoding the same, are provided. These proteins, herein termed LGR7 and LGR8, are orphan leucine-repeat-containing, G protein-coupled receptors. These receptors have a wide and a unique tissue expression pattern. The receptors, particularly soluble fragments thereof, are useful as therapeutic agents capable of inhibiting the action of relaxin and InsL3. The receptors and fragments thereof also find use in the screening and design of relaxin agonists and antagonists. Conditions treatable with relaxin agonists or antagonists include prevention or induction of labor, treatment of endometriosis, treatment of skin conditions such as scleroderma that require collagen or extracellular matrix remodelling. Additionally, relaxin has been implicated in the dilation of blood vessels' smooth muscle cells directly and through release of nitric oxide and atrial natriuretic peptide. Relaxin has also been used in the treatment of severe chronic pain, particularly pain arising from stretching, swelling, or dislocation of tissues.

1 Claim, 13 Drawing Sheets

FIG. 1A

```
LGR8:         MIVFLVFKHLFSLRLITMFFLLHFIVLINVKDFALT                                                    36
LGR7:         MTSGSVFFYILIFGKYFSHGGG                                                                  22
DLGR3:
LSLGR:        MATMSGTTIVCLIYLTTMLGNSQGVNLKIESPSPPTLCSVEGTFHCDDGMLQCVLMGSKCDGVSDCENGM
              DESVETCGCLQSEFQCNHTTCIDKILRCDRNDDCSNGLDERECDIYICPLGTHVKWHNHFCVPRDKQCDF
              LDDCGDNSDEKICERRECVATEFKCNNSQCVAFGNLCDGLVDCVDGSDEDQVACDSDKYFQCAEGSLIKK
              EFVCDGWVDCKLTFADELNCKLCDEDDFRCSDTRCIQKSNVCDGYCDCKTCDDEEVCANNTYGCPMDTKY
              MCRSIYGEPRCIDKDNVCNMINDCRDGNVGTDEYYCSNDSECKNFQAAMGFFYCPEERCLAKHLYCDLHP
              DCINGEDEQSCLAPPKCSQDEFQCHHGKCIPISKRCDSVHDCVDWSDEMNCENHQCAANMKSCLSGHCIE
              EHKWCNFHRECPDGSDEKDCDPRPVCEANQFRCKNGQCIDPLQVCVKGDKYDGCADQSHLINCSQHICLE
              GQFRCRKSFCINQTKVCDGTVDCLQGMWDENNCRYWCPHGQAICQCEGVTMDCTGQKLKEMPVQQM        563

LGR8:   37    QGSMITPSCQKGYFPCGNLTKCLPRAFHCDGKDDCGNGADEENGCDTSGWATIFGTVHGNANSV---     100
LGR7:   23    ----QDVKCSLGYFPCGNITKCLPQLLHCNGVDDCGNQADEDNCGDNNGWSMQFDKYFASYYKMTSQYPF   88
DLGR3:  1     ---------KCPGGYFHCNTTAQCVPQRANCDGSVDCDDASDEVNCVNEVDAKYWDHLYRKQPFGRHDNLRI 63
LSLGR:
                                              → LRR1                        → LRR2

LGR8:   101   -ALTQECFLKQYPQCCDCKETELECVNGDLKSVPMISNNVTLLSLKKNKIHSLPDKVFIKYTKLKKIFLQ   169
LGR7:   89    EAETPECLVGSVPVQCLCQGLELDCDETNLRAVPSVSSNVTAMSLQWNLIRKLPPDCFKNYHDLQKLYLQ   158
DLGR3:  64    ----GECLWPNENFSCPCRGDEILCRFQQLTDIPERLPQHDLATLDLTGNNFETIHETFFSELPDVDSLV   129
LSLGR:
                              → LRR3                        → LRR4                        → LRR5

LGR8:   170   HNCIRHISRKAFFGLCNLQILYLNHNCITTLRPGIFKDLHQLTWLILDDNPITRISQRLFT-GLNSLFFLS  239
LGR7:   159   NNKITSISIYAFRGLNSLTKLYLSHNRITFLKPGVFEDLHRLEWLIIEDNHLSRISPPTFY-GLNSLILLV  228
DLGR3:  130   LKFCSIREIASHAFDRLADNPLRTLYMDDNKLPHLPEHFFPEGNQLSILILARNHLHHLKRSD-FLNLQKLQE  201
LSLGR:  564   ------------------------------EEDLSKLMIGDNLLNLTSTTFSATYYDKVTYLD          589
                              → LRR6                        → LRR7                        → LRR8

LGR8:   240   MVNNYLEALP-KQMCAQMPQLNWVDLEGNRIKYLTNSTFLSCDSLTVLFLPRNQIGFVPEKTFSSLKNLG   308
LGR7:   229   LMNNVLTRLPDKPLCQHMPRLHWLDLEGNHIHNLRNLTFISCSNLTVLVMRKNKINHLNENTFAPLQKLD   298
DLGR3:  202   LDLRGNRIGNFEAEVFARLPNLEVLYLNENHLKRLDPDRFPRTLLNLHTLSLAYNQIEDIAANTFPFPRLR-  272
LSLGR:  590   LSRNHLTEIP-IYSFQNMWKLTHLNLADNNITSLKNGSLLGLSNLKQLHINGNKIETIEEDTFSSMIHLT   658
```

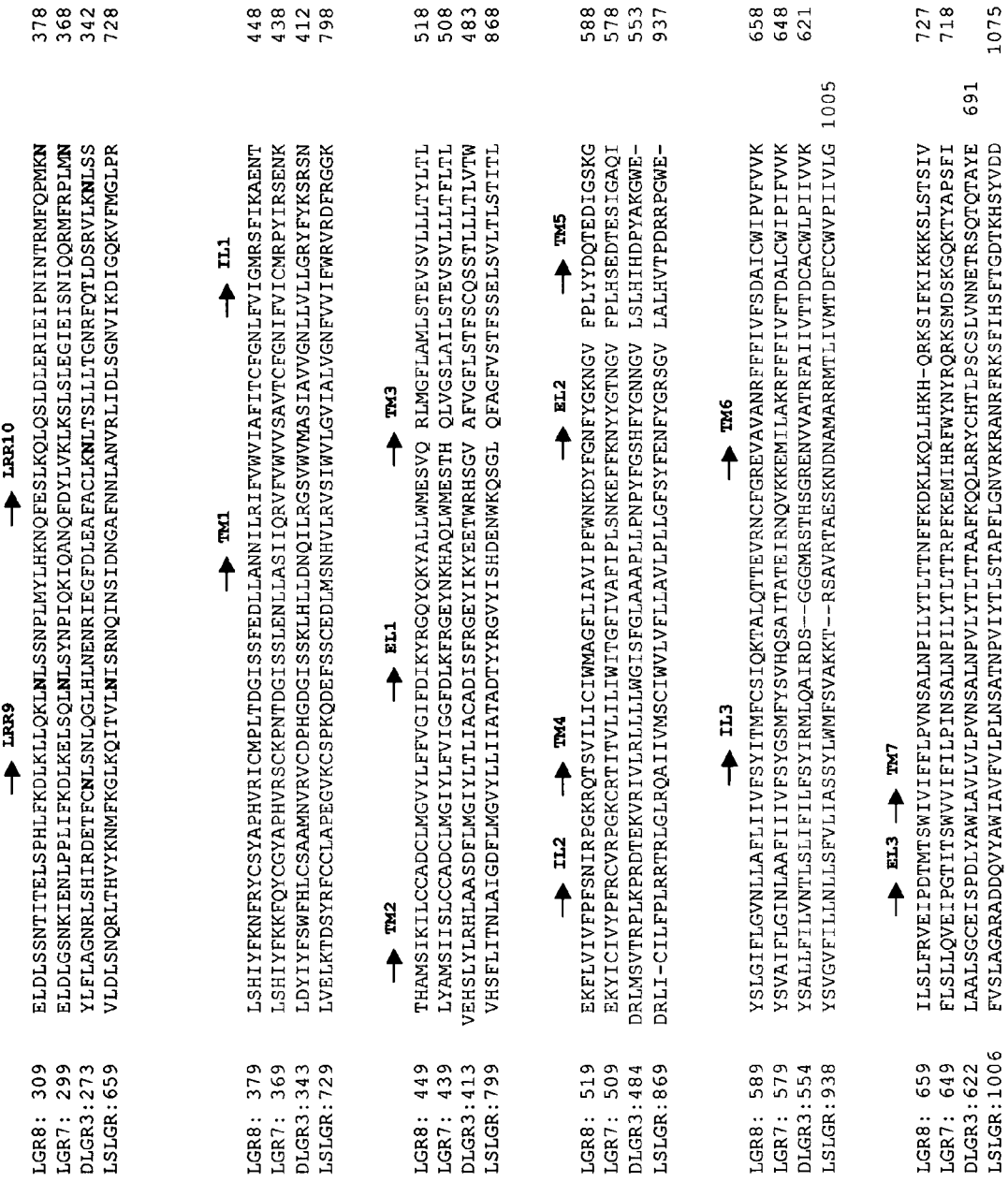

FIG. 1C

```
LGR8:  729  WIEDSSSLKLGVLNKITLGDSIMKPVS*                     755
LGR7:  719  WVEMWPLQEMPPELMKPDLFTYPCEMSLISQSTRLNSYS*         757
DLGR3: 692  SGLSVSLAHLGGGVGGGSGRKRMSHRQMSYL*                 722
LSLGR:1076  GTTHSYCEKKSPYRQLELKRLRSLNSSPPMYYNTELHSDS*       1115
```

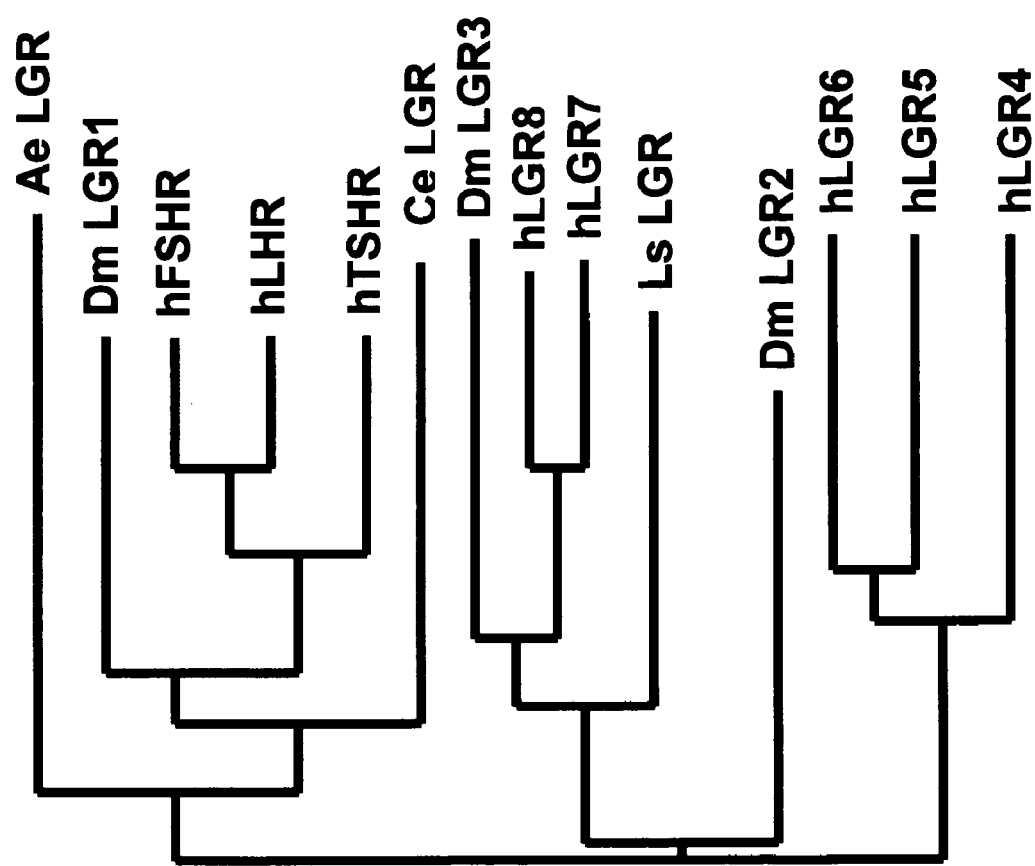

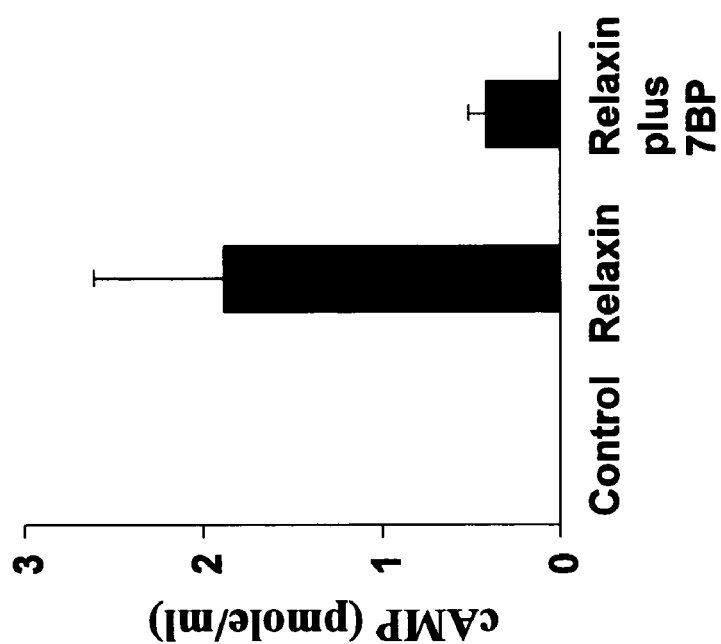
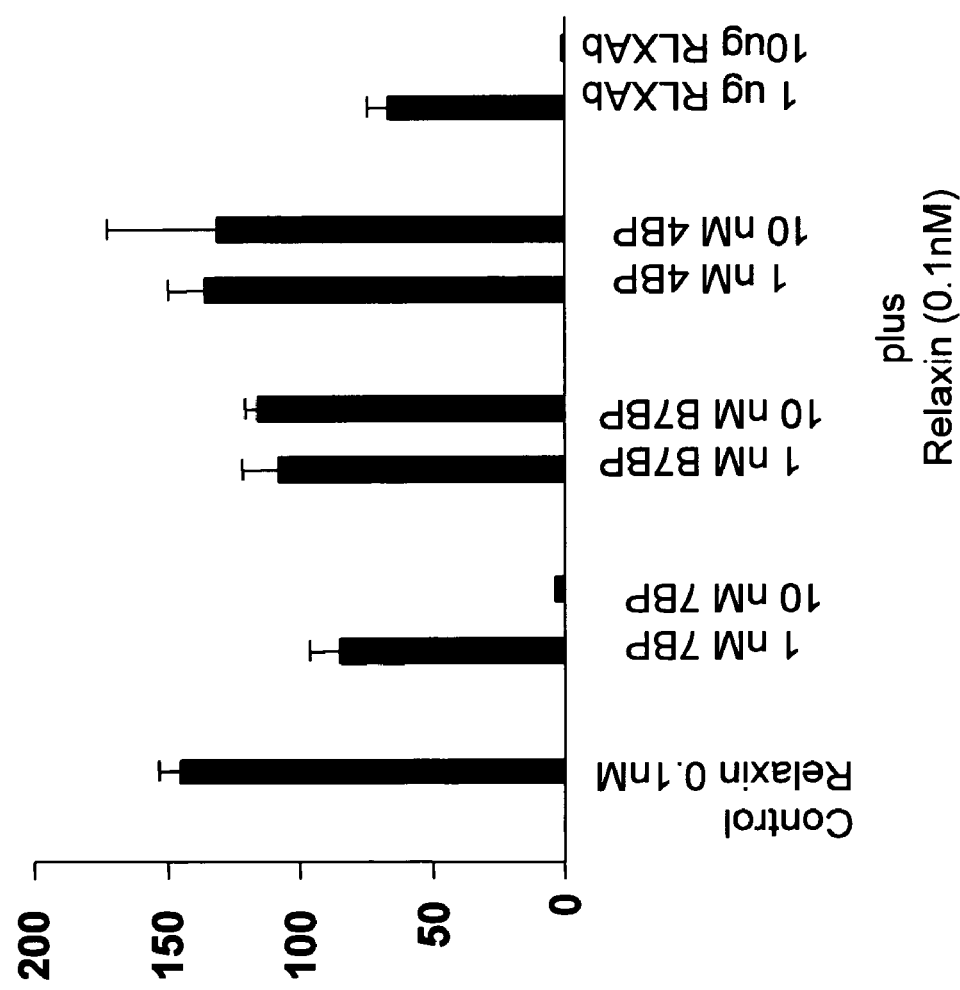

SEQUENCE LISTING

<160> NUMBER OF SEQ ID NOS: 4

<210> SEQ ID NO 1
<211> LENGTH: 2838
<212> TYPE: DNA
<213> ORGANISM: H. sapiens
<220> FEATURE:
<221> NAME/KEY: CDS
<222> LOCATION: (107)...(2369)

<400> SEQUENCE: 1

```
actcactata gggctcgagc ggccgcccgg gcaggtgaac ttactacatc agaactcctg     60
ctgaggtata agaggatacg tctaataact caattgctgt aaacct atg att gtt        115
                                                Met Ile Val
                                                  1 ttt ctg gtt ttt aaa cat ctc ttc agc ctc aga ttg att aca atg ttc      163
Phe Leu Val Phe Lys His Leu Phe Ser Leu Arg Leu Ile Thr Met Phe
 5                  10                  15 ttt cta ctt cat ttc atc gtt ctg atc aat gtc aaa gat ttt gca ctg      211
Phe Leu Leu His Phe Ile Val Leu Ile Asn Val Lys Asp Phe Ala Leu
         20                  25                  30              35 act caa ggt agc atg atc act cct tca tgc caa aaa gga tat ttt ccc      259
Thr Gln Gly Ser Met Ile Thr Pro Ser Cys Gln Lys Gly Tyr Phe Pro
                 40                  45                  50 tgt ggg aat ctt acc aag tgc tta ccc cga gct ttt cac tgt gat ggc      307
Cys Gly Asn Leu Thr Lys Cys Leu Pro Arg Ala Phe His Cys Asp Gly
             55                  60                  65 aag gat gac tgt ggg aac ggg gcg gac gaa gag aac tgt ggt gac act      355
Lys Asp Asp Cys Gly Asn Gly Ala Asp Glu Glu Asn Cys Gly Asp Thr
 70                  75                  80 agt gga tgg gcg acc ata ttt ggc aca gtg cat gga aat gct aac agc      403
Ser Gly Trp Ala Thr Ile Phe Gly Thr Val His Gly Asn Ala Asn Ser
     85                  90                  95 gtg gcc tta aca cag gag tgc ttt cta aaa cag tat cca caa tgc tgt      451
Val Ala Leu Thr Gln Glu Cys Phe Leu Lys Gln Tyr Pro Gln Cys Cys
100                 105                 110                 115 gac tgc aaa gaa act gaa ttg gaa tgt gta aat ggt gac tta aag tct      499
Asp Cys Lys Glu Thr Glu Leu Glu Cys Val Asn Gly Asp Leu Lys Ser
                 120                 125                 130 gtg ccg atg att tct aac aat gtg aca tta ctg tct ctt aag aaa aac      547
Val Pro Met Ile Ser Asn Asn Val Thr Leu Leu Ser Leu Lys Lys Asn
             135                 140                 145 aaa atc cac agt ctt cca gat aaa gtt ttc atc aaa tac aca aaa ctt      595
Lys Ile His Ser Leu Pro Asp Lys Val Phe Ile Lys Tyr Thr Lys Leu
             150                 155                 160 aaa aag ata ttt ctt cag cat aat tgc att aga cac ata tcc agg aaa      643
Lys Lys Ile Phe Leu Gln His Asn Cys Ile Arg His Ile Ser Arg Lys
165                 170                 175 gca ttt ttt gga tta tgt aat ctg caa ata tta tat ctc aac cac aac      691
Ala Phe Phe Gly Leu Cys Asn Leu Gln Ile Leu Tyr Leu Asn His Asn
180                 185                 190                 195 tgc atc aca acc ctc aga cct gga ata ttc aaa gac tta cat cag cta      739
Cys Ile Thr Thr Leu Arg Pro Gly Ile Phe Lys Asp Leu His Gln Leu
                 200                 205                 210 act tgg cta att cta gat gac aat cca ata acc aga att tca cag cgc      787
Thr Trp Leu Ile Leu Asp Asp Asn Pro Ile Thr Arg Ile Ser Gln Arg
             215                 220                 225 ttg ttt acg gga tta aat tcc ttg ttt ttc ctg tct atg gtt aat aac      835
Leu Phe Thr Gly Leu Asn Ser Leu Phe Phe Leu Ser Met Val Asn Asn
             230                 235                 240 tac tta gaa gct ctt ccc aag cag atg tgt gcc caa atg cct caa ctc      883
Tyr Leu Glu Ala Leu Pro Lys Gln Met Cys Ala Gln Met Pro Gln Leu
245                 250                 255 aac tgg gtg gat ttg gaa ggc aat aga ata aag tat ctc aca aat tct      931
Asn Trp Val Asp Leu Glu Gly Asn Arg Ile Lys Tyr Leu Thr Asn Ser
260                 265                 270                 275 acg ttt ctg tcg tgc gat tcg ctc aca gtg ctg ttt ctg cct aga aat      979
Thr Phe Leu Ser Cys Asp Ser Leu Thr Val Leu Phe Leu Pro Arg Asn
                 280                 285                 290
```

```
caa att ggt ttt gtt cca gag aag aca ttt tct tca tta aaa aat tta      1027
Gln Ile Gly Phe Val Pro Glu Lys Thr Phe Ser Ser Leu Lys Asn Leu
            295                 300                 305 gga gaa ctg gat ctg tct agc aat acg ata acg gag cta tca cct cac      1075
Gly Glu Leu Asp Leu Ser Ser Asn Thr Ile Thr Glu Leu Ser Pro His
        310                 315                 320 ctt ttt aaa gac ttg aag ctt cta caa aag ctg aac ctg tca tcc aat      1123
Leu Phe Lys Asp Leu Lys Leu Leu Gln Lys Leu Asn Leu Ser Ser Asn
    325                 330                 335 cct ctt atg tat ctt cac aag aac cag ttt gaa agt ctt aaa caa ctt      1171
Pro Leu Met Tyr Leu His Lys Asn Gln Phe Glu Ser Leu Lys Gln Leu
340                 345                 350                 355 cag tct cta gac ctg gaa agg ata gag att cca aat ata aac aca cga      1219
Gln Ser Leu Asp Leu Glu Arg Ile Glu Ile Pro Asn Ile Asn Thr Arg
            360                 365                 370 atg ttt caa ccc atg aag aat ctt tct cac att tat ttc aaa aac ttt      1267
Met Phe Gln Pro Met Lys Asn Leu Ser His Ile Tyr Phe Lys Asn Phe
        375                 380                 385 cga tac tgc tcc tat gct ccc cat gtc cga ata tgt atg ccc ttg acg      1315
Arg Tyr Cys Ser Tyr Ala Pro His Val Arg Ile Cys Met Pro Leu Thr
    390                 395                 400 gac ggc att tct tca ttt gag gac ctc ttg gct aac aat atc ctc aga      1363
Asp Gly Ile Ser Ser Phe Glu Asp Leu Leu Ala Asn Asn Ile Leu Arg
405                 410                 415 ata ttt gtc tgg gtt ata gct ttc att acc tgc ttt gga aat ctt ttt      1411
Ile Phe Val Trp Val Ile Ala Phe Ile Thr Cys Phe Gly Asn Leu Phe
            420                 425                 430                 435 gtc att ggc atg aga tct ttc att aaa gct gaa aat aca act cac gct      1459
Val Ile Gly Met Arg Ser Phe Ile Lys Ala Glu Asn Thr Thr His Ala
        440                 445                 450 atg tcc atc aaa atc ctt tgt tgt gct gat tgc ctg atg ggt gtt tac      1507
Met Ser Ile Lys Ile Leu Cys Cys Ala Asp Cys Leu Met Gly Val Tyr
    455                 460                 465 ttg ttc ttt gtt ggc att ttc gat ata aaa tac cga ggg cag tat cag      1555
Leu Phe Phe Val Gly Ile Phe Asp Ile Lys Tyr Arg Gly Gln Tyr Gln
    470                 475                 480 aag tat gcc ttg ctg tgg atg gag agc gtg cag tgc cgc ctc atg ggg      1603
Lys Tyr Ala Leu Leu Trp Met Glu Ser Val Gln Cys Arg Leu Met Gly
485                 490                 495 ttc ctg gcc atg ctg tcc acc gaa gtc tct gtt ctg cta ctg acc tac      1651
Phe Leu Ala Met Leu Ser Thr Glu Val Ser Val Leu Leu Leu Thr Tyr
500                 505                 510                 515 ttg act ttg gag aag ttc ctg gtc att gtc ttc ccc ttc agt aac att      1699
Leu Thr Leu Glu Lys Phe Leu Val Ile Val Phe Pro Phe Ser Asn Ile
            520                 525                 530 cga cct gga aaa cgg cag acc tca gtc atc ctc att tgc atc tgg atg      1747
Arg Pro Gly Lys Arg Gln Thr Ser Val Ile Leu Ile Cys Ile Trp Met
        535                 540                 545 gcg gga ttt tta ata gct gta att cca ttt tgg aat aag gat tat ttt      1795
Ala Gly Phe Leu Ile Ala Val Ile Pro Phe Trp Asn Lys Asp Tyr Phe
    550                 555                 560 gga aac ttt tat ggg aaa aat gga gta tgt ttc cca ctt tat tat gac      1843
Gly Asn Phe Tyr Gly Lys Asn Gly Val Cys Phe Pro Leu Tyr Tyr Asp
    565                 570                 575 caa aca gaa gat att gga agc aaa ggg tat tct ctt gga att ttc cta      1891
Gln Thr Glu Asp Ile Gly Ser Lys Gly Tyr Ser Leu Gly Ile Phe Leu
580                 585                 590                 595 ggt gtg aac ttg ctg gct ttt ctc atc att gtg ttt tcc tat att act      1939
Gly Val Asn Leu Leu Ala Phe Leu Ile Ile Val Phe Ser Tyr Ile Thr
```

-continued

```
                     600                 605                 610
atg ttc tgt tcc att caa aaa acc gcc ttg cag acc aca gaa gta agg      1987
Met Phe Cys Ser Ile Gln Lys Thr Ala Leu Gln Thr Thr Glu Val Arg
            615                 620                 625 aat tgt ttt gga aga gag gtg gct gtt gca aat cgt ttc ttt ttt ata      2035
Asn Cys Phe Gly Arg Glu Val Ala Val Ala Asn Arg Phe Phe Phe Ile
            630                 635                 640 gtg ttc tct gat gcc atc tgc tgg att cct gta ttt gta gtt aaa atc      2083
Val Phe Ser Asp Ala Ile Cys Trp Ile Pro Val Phe Val Val Lys Ile
    645                 650                 655 ctt tcc ctc ttc cgg gtg gaa ata cca gac aca atg act tcc tgg ata      2131
Leu Ser Leu Phe Arg Val Glu Ile Pro Asp Thr Met Thr Ser Trp Ile
660                 665                 670                 675 gtg att ttt ttc ctt cca gtt aac agt gct ttg aat cca atc ctc tat      2179
Val Ile Phe Phe Leu Pro Val Asn Ser Ala Leu Asn Pro Ile Leu Tyr
            680                 685                 690 act ctc aca acc aac ttt ttt aag gac aag ttg aaa cag ctg ctg cac      2227
Thr Leu Thr Thr Asn Phe Phe Lys Asp Lys Leu Lys Gln Leu Leu His
            695                 700                 705 aaa cat cag agg aaa tca att ttc aaa att aaa aaa aaa agt tta tct      2275
Lys His Gln Arg Lys Ser Ile Phe Lys Ile Lys Lys Lys Ser Leu Ser
    710                 715                 720 aca tcc att gtg tgg ata gag gac tcc tct tcc ctg aaa ctt ggg gtt      2323
Thr Ser Ile Val Trp Ile Glu Asp Ser Ser Ser Leu Lys Leu Gly Val
    725                 730                 735 ttg aac aaa ata aca ctt gga gac agt ata atg aaa cca gtt tcc t        2369
Leu Asn Lys Ile Thr Leu Gly Asp Ser Ile Met Lys Pro Val Ser
740                 745                 750 agcaatcatt ttggatcact ggactttcag tggactacct aaaacagggg acagcttttg    2429
gaagatgaca tctgcaatgc ttttcatctt taccaacggc aagcctttct gcacagagag    2489
cacagcagaa tggctcctgt cactgcattc caatggcagc tgtactatct accaaccatg    2549
ctgaggacag caccaaaggt tcctctcctc accccacatg cctgaaaagc acatgtgaat    2609
tcgtgtatag tgggctgagg tgcagctgat ctctagctaa tcaacacaac ccaccaacaa    2669
atgaccacag gttggcactg tgtggtcttt cacatcgggt tgcactgtcc atgaaataga    2729
aacactcaca acatctgatt ccagtgtggc cataataaca gaaatctaac aactctttcc    2789
ttgccttttc aatatcaaat aaaaccatca gcatcctgct ggattgata              2838
```

<210> SEQ ID NO 2
<211> LENGTH: 754
<212> TYPE: PRT
<213> ORGANISM: H. sapiens

<400> SEQUENCE: 2

```
Met Ile Val Phe Leu Val Phe Lys His Leu Phe Ser Leu Arg Leu Ile
 1               5                  10                  15

Thr Met Phe Phe Leu Leu His Phe Ile Val Leu Ile Asn Val Lys Asp
            20                  25                  30

Phe Ala Leu Thr Gln Gly Ser Met Ile Thr Pro Ser Cys Gln Lys Gly
        35                  40                  45

Tyr Phe Pro Cys Gly Asn Leu Thr Lys Cys Leu Pro Arg Ala Phe His
    50                  55                  60

Cys Asp Gly Lys Asp Asp Cys Gly Asn Gly Ala Asp Glu Glu Asn Cys
65                  70                  75                  80

Gly Asp Thr Ser Gly Trp Ala Thr Ile Phe Gly Thr Val His Gly Asn
                85                  90                  95
```

-continued

Ala Asn Ser Val Ala Leu Thr Gln Glu Cys Phe Leu Lys Gln Tyr Pro
              100                 105                 110

Gln Cys Cys Asp Cys Lys Glu Thr Glu Leu Glu Cys Val Asn Gly Asp
          115                 120                 125

Leu Lys Ser Val Pro Met Ile Ser Asn Asn Val Thr Leu Leu Ser Leu
    130                 135                 140

Lys Lys Asn Lys Ile His Ser Leu Pro Asp Lys Val Phe Ile Lys Tyr
145                 150                 155                 160

Thr Lys Leu Lys Lys Ile Phe Leu Gln His Asn Cys Ile Arg His Ile
                165                 170                 175

Ser Arg Lys Ala Phe Phe Gly Leu Cys Asn Leu Gln Ile Leu Tyr Leu
            180                 185                 190

Asn His Asn Cys Ile Thr Thr Leu Arg Pro Gly Ile Phe Lys Asp Leu
        195                 200                 205

His Gln Leu Thr Trp Leu Ile Leu Asp Asp Asn Pro Ile Thr Arg Ile
    210                 215                 220

Ser Gln Arg Leu Phe Thr Gly Leu Asn Ser Leu Phe Phe Leu Ser Met
225                 230                 235                 240

Val Asn Asn Tyr Leu Glu Ala Leu Pro Lys Gln Met Cys Ala Gln Met
                245                 250                 255

Pro Gln Leu Asn Trp Val Asp Leu Glu Gly Asn Arg Ile Lys Tyr Leu
            260                 265                 270

Thr Asn Ser Thr Phe Leu Ser Cys Asp Ser Leu Thr Val Leu Phe Leu
        275                 280                 285

Pro Arg Asn Gln Ile Gly Phe Val Pro Glu Lys Thr Phe Ser Ser Leu
    290                 295                 300

Lys Asn Leu Gly Glu Leu Asp Leu Ser Ser Asn Thr Ile Thr Glu Leu
305                 310                 315                 320

Ser Pro His Leu Phe Lys Asp Leu Lys Leu Leu Gln Lys Leu Asn Leu
                325                 330                 335

Ser Ser Asn Pro Leu Met Tyr Leu His Lys Asn Gln Phe Glu Ser Leu
            340                 345                 350

Lys Gln Leu Gln Ser Leu Asp Leu Glu Arg Ile Glu Ile Pro Asn Ile
        355                 360                 365

Asn Thr Arg Met Phe Gln Pro Met Lys Asn Leu Ser His Ile Tyr Phe
    370                 375                 380

Lys Asn Phe Arg Tyr Cys Ser Tyr Ala Pro His Val Arg Ile Cys Met
385                 390                 395                 400

Pro Leu Thr Asp Gly Ile Ser Ser Phe Glu Asp Leu Leu Ala Asn Asn
                405                 410                 415

Ile Leu Arg Ile Phe Val Trp Val Ile Ala Phe Ile Thr Cys Phe Gly
            420                 425                 430

Asn Leu Phe Val Ile Gly Met Arg Ser Phe Ile Lys Ala Glu Asn Thr
        435                 440                 445

Thr His Ala Met Ser Ile Lys Ile Leu Cys Cys Ala Asp Cys Leu Met
    450                 455                 460

Gly Val Tyr Leu Phe Phe Val Gly Ile Phe Asp Ile Lys Tyr Arg Gly
465                 470                 475                 480

Gln Tyr Gln Lys Tyr Ala Leu Leu Trp Met Glu Ser Val Gln Cys Arg
                485                 490                 495

Leu Met Gly Phe Leu Ala Met Leu Ser Thr Glu Val Ser Val Leu Leu
            500                 505                 510

```
Leu Thr Tyr Leu Thr Leu Glu Lys Phe Leu Val Ile Val Phe Pro Phe
            515                 520                 525

Ser Asn Ile Arg Pro Gly Lys Arg Gln Thr Ser Val Ile Leu Ile Cys
            530                 535                 540

Ile Trp Met Ala Gly Phe Leu Ala Val Ile Pro Phe Trp Asn Lys
545                 550                 555                 560

Asp Tyr Phe Gly Asn Phe Tyr Gly Lys Asn Gly Val Cys Phe Pro Leu
            565                 570                 575

Tyr Tyr Asp Gln Thr Glu Asp Ile Gly Ser Lys Gly Tyr Ser Leu Gly
            580                 585                 590

Ile Phe Leu Gly Val Asn Leu Ala Phe Leu Ile Val Phe Ser
            595                 600                 605

Tyr Ile Thr Met Phe Cys Ser Ile Gln Lys Thr Ala Leu Gln Thr Thr
            610                 615                 620

Glu Val Arg Asn Cys Phe Gly Arg Glu Val Ala Val Ala Asn Arg Phe
625                 630                 635                 640

Phe Phe Ile Val Phe Ser Asp Ala Ile Cys Trp Ile Pro Val Phe Val
            645                 650                 655

Val Lys Ile Leu Ser Leu Phe Arg Val Glu Ile Pro Asp Thr Met Thr
            660                 665                 670

Ser Trp Ile Val Ile Phe Phe Leu Pro Val Asn Ser Ala Leu Asn Pro
            675                 680                 685

Ile Leu Tyr Thr Leu Thr Thr Asn Phe Phe Lys Asp Lys Leu Lys Gln
            690                 695                 700

Leu Leu His Lys His Gln Arg Lys Ser Ile Phe Lys Ile Lys Lys Lys
705                 710                 715                 720

Ser Leu Ser Thr Ser Ile Val Trp Ile Glu Asp Ser Ser Leu Lys
            725                 730                 735

Leu Gly Val Leu Asn Lys Ile Thr Leu Gly Asp Ser Ile Met Lys Pro
            740                 745                 750

Val Ser

<210> SEQ ID NO 3
<211> LENGTH: 1115
<212> TYPE: PRT
<213> ORGANISM: H. sapiens

<400> SEQUENCE: 3

Met Ala Thr Met Ser Gly Thr Thr Ile Val Cys Leu Ile Tyr Leu Thr
1               5                   10                  15

Thr Met Leu Gly Asn Ser Gln Gly Val Asn Leu Lys Ile Glu Ser Pro
            20                  25                  30

Ser Pro Pro Thr Leu Cys Ser Val Glu Gly Thr Phe His Cys Asp Asp
            35                  40                  45

Gly Met Leu Gln Cys Val Leu Met Gly Ser Lys Cys Asp Gly Val Ser
            50                  55                  60

Asp Cys Glu Asn Gly Met Asp Glu Ser Val Glu Thr Cys Gly Cys Leu
65                  70                  75                  80

Gln Ser Glu Phe Gln Cys Asn His Thr Thr Cys Ile Asp Lys Ile Leu
            85                  90                  95

Arg Cys Asp Arg Asn Asp Asp Cys Ser Asn Gly Leu Asp Glu Arg Glu
            100                 105                 110

Cys Asp Ile Tyr Ile Cys Pro Leu Gly Thr His Val Lys Trp His Asn
            115                 120                 125
```

```
His Phe Cys Val Pro Arg Asp Lys Gln Cys Asp Phe Leu Asp Asp Cys
        130                 135                 140

Gly Asp Asn Ser Asp Glu Lys Ile Cys Glu Arg Arg Glu Cys Val Ala
145                 150                 155                 160

Thr Glu Phe Lys Cys Asn Asn Ser Gln Cys Val Ala Phe Gly Asn Leu
                165                 170                 175

Cys Asp Gly Leu Val Asp Cys Val Asp Gly Ser Asp Glu Asp Gln Val
            180                 185                 190

Ala Cys Asp Ser Asp Lys Tyr Phe Gln Cys Ala Glu Gly Ser Leu Ile
        195                 200                 205

Lys Lys Glu Phe Val Cys Asp Gly Trp Val Asp Cys Lys Leu Thr Phe
    210                 215                 220

Ala Asp Glu Leu Asn Cys Lys Leu Cys Asp Glu Asp Phe Arg Cys
225                 230                 235                 240

Ser Asp Thr Arg Cys Ile Gln Lys Ser Asn Val Cys Asp Gly Tyr Cys
                245                 250                 255

Asp Cys Lys Thr Cys Asp Asp Glu Val Cys Ala Asn Asn Thr Tyr
                260                 265                 270

Gly Cys Pro Met Asp Thr Lys Tyr Met Cys Arg Ser Ile Tyr Gly Glu
            275                 280                 285

Pro Arg Cys Ile Asp Lys Asp Asn Val Cys Asn Met Ile Asn Asp Cys
    290                 295                 300

Arg Asp Gly Asn Val Gly Thr Asp Glu Tyr Tyr Cys Ser Asn Asp Ser
305                 310                 315                 320

Glu Cys Lys Asn Phe Gln Ala Ala Met Gly Phe Phe Tyr Cys Pro Glu
                325                 330                 335

Glu Arg Cys Leu Ala Lys His Leu Tyr Cys Asp Leu His Pro Asp Cys
            340                 345                 350

Ile Asn Gly Glu Asp Glu Gln Ser Cys Leu Ala Pro Pro Lys Cys Ser
                355                 360                 365

Gln Asp Glu Phe Gln Cys His His Gly Lys Cys Ile Pro Ile Ser Lys
    370                 375                 380

Arg Cys Asp Ser Val His Asp Cys Val Asp Trp Ser Asp Glu Met Asn
385                 390                 395                 400

Cys Glu Asn His Gln Cys Ala Ala Asn Met Lys Ser Cys Leu Ser Gly
                405                 410                 415

His Cys Ile Glu Glu His Lys Trp Cys Asn Phe His Arg Glu Cys Pro
            420                 425                 430

Asp Gly Ser Asp Glu Lys Asp Cys Asp Pro Arg Pro Val Cys Glu Ala
        435                 440                 445

Asn Gln Phe Arg Cys Lys Asn Gly Gln Cys Ile Asp Pro Leu Gln Val
    450                 455                 460

Cys Val Lys Gly Asp Lys Tyr Asp Gly Cys Ala Asp Gln Ser His Leu
465                 470                 475                 480

Ile Asn Cys Ser Gln His Ile Cys Leu Glu Gly Gln Phe Arg Cys Arg
                485                 490                 495

Lys Ser Phe Cys Ile Asn Gln Thr Lys Val Cys Asp Gly Thr Val Asp
            500                 505                 510

Cys Leu Gln Gly Met Trp Asp Glu Asn Asn Cys Arg Tyr Trp Cys Pro
        515                 520                 525

His Gly Gln Ala Ile Cys Gln Cys Glu Gly Val Thr Met Asp Cys Thr
    530                 535                 540

Gly Gln Lys Leu Lys Glu Met Pro Val Gln Gln Met Glu Glu Asp Leu
```

-continued

```
            545                 550                 555                 560
        Ser Lys Leu Met Ile Gly Asp Asn Leu Leu Asn Leu Thr Ser Thr Thr
                        565                 570                 575
        Phe Ser Ala Thr Tyr Tyr Asp Lys Val Thr Tyr Leu Asp Leu Ser Arg
                        580                 585                 590
        Asn His Leu Thr Glu Ile Pro Ile Tyr Ser Phe Gln Asn Met Trp Lys
                        595                 600                 605
        Leu Thr His Leu Asn Leu Ala Asp Asn Asn Ile Thr Ser Leu Lys Asn
                        610                 615                 620
        Gly Ser Leu Leu Gly Leu Ser Asn Leu Lys Gln Leu His Ile Asn Gly
        625                 630                 635                 640
        Asn Lys Ile Glu Thr Ile Glu Glu Asp Thr Phe Ser Ser Met Ile His
                        645                 650                 655
        Leu Thr Val Leu Asp Leu Ser Asn Gln Arg Leu Thr His Val Tyr Lys
                        660                 665                 670
        Asn Met Phe Lys Gly Leu Lys Gln Ile Thr Val Leu Asn Ile Ser Arg
                        675                 680                 685
        Asn Gln Ile Asn Ser Ile Asp Asn Gly Ala Phe Asn Asn Leu Ala Asn
                        690                 695                 700
        Val Arg Leu Ile Asp Leu Ser Gly Asn Val Ile Lys Asp Ile Gly Gln
        705                 710                 715                 720
        Lys Val Phe Met Gly Leu Pro Arg Leu Val Glu Leu Lys Thr Asp Ser
                        725                 730                 735
        Tyr Arg Phe Cys Cys Leu Ala Pro Glu Gly Val Lys Cys Ser Pro Lys
                        740                 745                 750
        Gln Asp Glu Phe Ser Ser Cys Glu Asp Leu Met Ser Asn His Val Leu
                        755                 760                 765
        Arg Val Ser Ile Trp Val Leu Gly Val Ile Ala Leu Val Gly Asn Phe
                        770                 775                 780
        Val Val Ile Phe Trp Arg Val Arg Asp Phe Arg Gly Gly Lys Val His
        785                 790                 795                 800
        Ser Phe Leu Ile Thr Asn Leu Ala Ile Gly Asp Phe Leu Met Gly Val
                        805                 810                 815
        Tyr Leu Leu Ile Ile Ala Thr Ala Asp Thr Tyr Tyr Arg Gly Val Tyr
                        820                 825                 830
        Ile Ser His Asp Glu Asn Trp Lys Gln Ser Gly Leu Cys Gln Phe Ala
                        835                 840                 845
        Gly Phe Val Ser Thr Phe Ser Ser Glu Leu Ser Val Leu Thr Leu Ser
                        850                 855                 860
        Thr Ile Thr Leu Asp Arg Leu Ile Cys Ile Leu Phe Pro Leu Arg Arg
        865                 870                 875                 880
        Thr Arg Leu Gly Leu Arg Gln Ala Ile Ile Val Met Ser Cys Ile Trp
                        885                 890                 895
        Val Leu Val Phe Leu Leu Ala Val Leu Pro Leu Leu Gly Phe Ser Tyr
                        900                 905                 910
        Phe Glu Asn Phe Tyr Gly Arg Ser Gly Val Cys Leu Ala Leu His Val
                        915                 920                 925
        Thr Pro Asp Arg Arg Pro Gly Trp Glu Tyr Ser Val Gly Val Phe Ile
                        930                 935                 940
        Leu Leu Asn Leu Leu Ser Phe Val Leu Ile Ala Ser Ser Tyr Leu Trp
        945                 950                 955                 960
        Met Phe Ser Val Ala Lys Lys Thr Arg Ser Ala Val Arg Thr Ala Glu
                        965                 970                 975
```

```
Ser Lys Asn Asp Asn Ala Met Ala Arg Arg Met Thr Leu Ile Val Met
            980                 985                 990

Thr Asp Phe Cys Cys Trp Val Pro Ile Ile Val Leu Gly Phe Val Ser
        995                 1000                1005

Leu Ala Gly Ala Arg Ala Asp Asp Gln Val Tyr Ala Trp Ile Ala Val
    1010                1015                1020

Phe Val Leu Pro Leu Asn Ser Ala Thr Asn Pro Val Ile Tyr Thr Leu
1025                1030                1035                1040

Ser Thr Ala Pro Phe Leu Gly Asn Val Arg Lys Arg Ala Asn Arg Phe
                1045                1050                1055

Arg Lys Ser Phe Ile His Ser Phe Thr Gly Asp Thr Lys His Ser Tyr
            1060                1065                1070

Val Asp Asp Gly Thr Thr His Ser Tyr Cys Glu Lys Lys Ser Pro Tyr
        1075                1080                1085

Arg Gln Leu Glu Leu Lys Arg Leu Arg Ser Leu Asn Ser Ser Pro Pro
    1090                1095                1100

Met Tyr Tyr Asn Thr Glu Leu His Ser Asp Ser
1105                1110                1115

<210> SEQ ID NO 4
<211> LENGTH: 722
<212> TYPE: PRT
<213> ORGANISM: H. sapiens

<400> SEQUENCE: 4

Lys Cys Pro Gly Gly Tyr Phe His Cys Asn Thr Thr Ala Gln Cys Val
1               5                   10                  15

Pro Gln Arg Ala Asn Cys Asp Gly Ser Val Asp Cys Asp Asp Ala Ser
            20                  25                  30

Asp Glu Val Asn Cys Val Asn Glu Val Asp Ala Lys Tyr Trp Asp His
        35                  40                  45

Leu Tyr Arg Lys Gln Pro Phe Gly Arg His Asp Asn Leu Arg Ile Gly
    50                  55                  60

Glu Cys Leu Trp Pro Asn Glu Asn Phe Ser Cys Pro Cys Arg Gly Asp
65                  70                  75                  80

Glu Ile Leu Cys Arg Phe Gln Gln Leu Thr Asp Ile Pro Glu Arg Leu
                85                  90                  95

Pro Gln His Asp Leu Ala Thr Leu Asp Leu Thr Gly Asn Asn Phe Glu
            100                 105                 110

Thr Ile His Glu Thr Phe Phe Ser Glu Leu Pro Asp Val Asp Ser Leu
        115                 120                 125

Val Leu Lys Phe Cys Ser Ile Arg Glu Ile Ala Ser His Ala Phe Asp
    130                 135                 140

Arg Leu Ala Asp Asn Pro Leu Arg Thr Leu Tyr Met Asp Asp Asn Lys
145                 150                 155                 160

Leu Pro His Leu Pro Glu His Phe Phe Pro Glu Gly Asn Gln Leu Ser
                165                 170                 175

Ile Leu Ile Leu Ala Arg Asn His Leu His His Leu Lys Arg Ser Asp
            180                 185                 190

Phe Leu Asn Leu Gln Lys Leu Gln Glu Leu Asp Leu Arg Gly Asn Arg
        195                 200                 205

Ile Gly Asn Phe Glu Ala Glu Val Phe Ala Arg Leu Pro Asn Leu Glu
    210                 215                 220

Val Leu Tyr Leu Asn Glu Asn His Leu Lys Arg Leu Asp Pro Asp Arg
```

-continued

```
        225                 230                 235                 240
Phe Pro Arg Thr Leu Leu Asn Leu His Thr Leu Ser Leu Ala Tyr Asn
                245                 250                 255
Gln Ile Glu Asp Ile Ala Ala Asn Thr Phe Pro Phe Pro Arg Leu Arg
                260                 265                 270
Tyr Leu Phe Leu Ala Gly Asn Arg Leu Ser His Ile Arg Asp Glu Thr
                275                 280                 285
Phe Cys Asn Leu Ser Asn Leu Gln Gly Leu His Leu Asn Glu Asn Arg
        290                 295                 300
Ile Glu Gly Phe Asp Leu Glu Ala Phe Ala Cys Leu Lys Asn Leu Thr
305                 310                 315                 320
Ser Leu Leu Leu Thr Gly Asn Arg Phe Gln Thr Leu Asp Ser Arg Val
                325                 330                 335
Leu Lys Asn Leu Ser Ser Leu Asp Tyr Ile Tyr Phe Ser Trp Phe His
                340                 345                 350
Leu Cys Ser Ala Ala Met Asn Val Arg Val Cys Asp Pro His Gly Asp
                355                 360                 365
Gly Ile Ser Ser Lys Leu His Leu Leu Asp Asn Gln Ile Leu Arg Gly
        370                 375                 380
Ser Val Trp Val Met Ala Ser Ile Ala Val Val Gly Asn Leu Leu Val
385                 390                 395                 400
Leu Leu Gly Arg Tyr Phe Tyr Lys Ser Arg Ser Asn Val Glu His Ser
                405                 410                 415
Leu Tyr Leu Arg His Leu Ala Ala Ser Asp Phe Leu Met Gly Ile Tyr
                420                 425                 430
Leu Thr Leu Ile Ala Cys Ala Asp Ile Ser Phe Arg Gly Glu Tyr Ile
                435                 440                 445
Lys Tyr Glu Glu Thr Trp Arg His Ser Gly Val Cys Ala Phe Val Gly
        450                 455                 460
Phe Leu Ser Thr Phe Ser Cys Gln Ser Ser Thr Leu Leu Leu Thr Leu
465                 470                 475                 480
Val Thr Trp Asp Arg Leu Met Ser Val Thr Arg Pro Leu Lys Pro Arg
                485                 490                 495
Asp Thr Glu Lys Val Arg Ile Val Leu Arg Leu Leu Leu Trp Gly
                500                 505                 510
Ile Ser Phe Gly Leu Ala Ala Ala Pro Leu Leu Pro Asn Pro Tyr Phe
        515                 520                 525
Gly Ser His Phe Tyr Gly Asn Asn Gly Val Cys Leu Ser Leu His Ile
        530                 535                 540
His Asp Pro Tyr Ala Lys Gly Trp Glu Tyr Ser Ala Leu Leu Phe Ile
545                 550                 555                 560
Leu Val Asn Thr Leu Ser Leu Ile Phe Ile Leu Phe Ser Tyr Ile Arg
                565                 570                 575
Met Leu Gln Ala Ile Arg Asp Ser Gly Gly Met Arg Ser Thr His
                580                 585                 590
Ser Gly Arg Glu Asn Val Val Ala Thr Arg Phe Ala Ile Ile Val Thr
                595                 600                 605
Thr Asp Cys Ala Cys Trp Leu Pro Ile Ile Val Val Lys Leu Ala Ala
        610                 615                 620
Leu Ser Gly Cys Glu Ile Ser Pro Asp Leu Tyr Ala Trp Leu Ala Val
625                 630                 635                 640
Leu Val Leu Pro Val Asn Ser Ala Leu Asn Pro Val Leu Tyr Thr Leu
                645                 650                 655
```

```
Thr Thr Ala Ala Phe Lys Gln Gln Leu Arg Arg Tyr Cys His Thr Leu
            660                 665                 670

Pro Ser Cys Ser Leu Val Asn Asn Glu Thr Arg Ser Gln Thr Gln Thr
        675                 680                 685

Ala Tyr Glu Ser Gly Leu Ser Val Ser Leu Ala His Leu Gly Gly Gly
        690                 695                 700

Val Gly Gly Gly Ser Gly Arg Lys Arg Met Ser His Arg Gln Met Ser
705                 710                 715                 720

Tyr Leu
```

SCREENING FOR AGENTS THAT MODULATE RELAXIN FUNCTION

BACKGROUND OF THE INVENTION

Relaxin is a pregnancy hormone discovered in 1926 (Hisaw (1926) *Proc. Soc. Exp. Biol. Med.* 23: 661-663), based on its ability to relax the public ligament in guinea pig. Mature human relaxin is a hormonal peptide of approximately 6000 daltons known to be responsible for remodelling the reproductive tract before parturition, thus facilitating the birth process. A concise review of relaxin was provided by Sherwood, D. in The Physiology of Reproduction, Chapter 16, "Relaxin", Knobil, E. and Neill, J., et al. (eds.), (Raven Press Ltd., New York), pp. 585-673 (1988). Relaxin has local autocrine and/or paracrine roles that contribute to connective tissue remodeling at the maternal-fetal interface during late pregnancy and at parturition, including an increase in the expression of the genes, proteins, and enzyme activities of the matrix metalloproteinases interstitial collagenase (MMP-1), stromelysin (MMP-3), and gelatinase B (MMP-9).

Two human gene forms of relaxin have been identified, (H1) and (H2) (Hudson et al. (1983) *Nature* 301:628-631; Hudson et al. (1984) *EMBO Journal* 3:2333-2339; U.S. Pat. Nos. 4,758,516 and 4,871,670). Only the H2 form is expressed in corpus luteum. The primary translation product of H2 relaxin is a preprorelaxin consisting of a 24 amino acid signal sequence followed by a B chain of about 29 amino acids, a connecting peptide of 104-107 amino acids, and an A chain of about 24 amino acids.

Although relaxin itself has been well-characterized for a number of years, it's receptor has remained elusive. To date, binding studies have had to rely on crude cellular extracts, which indicated that a specific binding molecule was present, but gave no clue as to its molecular identity. Relaxin binding sites have been reported in the reproductive tract (Kohsaka et al. (1998) *Biol Reprod* 59(4):991-9), as well as other tissues, including cardiac and other smooth muscle, and specific nuclei in the brain (Tan et al. (1999) *Br J Pharmacol* 127(1): 91-8).

During fetal development, the sexual dimorphic position of the gonads in mammals is dependent on the differential development of two ligaments. In males, growth of the gubernaculum and regression of the cranial suspensory ligament results in transabdominal descent of the testes. Impaired testicular descent (cryptorchidism) is a prevalent congenital abnormality in humans, found in 2% of male births. INSL3, also known as Leydig insulin-like peptide or relaxin-like factor (RLF), is one of the seven relaxin-like genes in humans known to be expressed in Leydig cells of fetal and adult testes as well as in theca and luteal cells of the postnatal ovary (Ivell (1997) *Rev. Reprod.* 2, 133-8). Male mice mutant for INSL3 exhibit bilateral abdominal cryptorchidism whereas female mice overexpressing INSL3 showed ovary descent and displayed bilateral inguinal hernia. Although INSL3 binds to gubernacular homogenates (Boockfor et al. (2001) *Reproduction* 122, 899-906) and induces growth of rat gubernaculum in whole organ cultures (Smith et al. (2001) *J. Pept. Sci.* 7, 495-501), the exact nature of the INSL3 receptor is unknown. A recent study indicated that transgene integration in crsp mice resulted in a 550-kb deletion located upstream of the Brca2 gene, leading to defective testis descent (Overbeek et al. (2001) *Genesis* 30, 26-35).

The identification and molecular characterization of relaxin receptors is of great scientific and clinical interest. Understanding of relaxin signaling mechanisms mediated by its receptor can provide new approaches for the regulation of relaxin target tissues during pregnant and non-pregnant states.

SUMMARY OF THE INVENTION

High affinity relaxin receptors, polypeptide compositions related thereto, as well as nucleotide compositions encoding the same, are provided. These proteins, herein termed LGR7 and LGR8, are orphan leucine-repeat-containing, G protein-coupled receptors, and are paralogs of gonadotropin and thyrotropin receptors. These receptors have a wide and unique tissue expression pattern. LGR8 is a receptor for InsL3, which has been shown to be important for testis descent. Treatment of antepartum animals with the soluble ligand-binding region of LGR7 has led to parturition delay. Thus, relaxin and lnsL3 signal through G protein-coupled receptors distinct from the related insulin family of ligands in regulating pregnancy-related processes.

The receptors, particularly soluble fragments thereof, are useful as therapeutic agents capable of inhibiting the action of relaxin. The receptors and fragments thereof also find use in the screening and design of relaxin agonists and antagonists. Conditions treatable with relaxin agonists or antagonists include prevention or induction of labor, treatment of endometriosis, treatment of skin conditions such as scleroderma that. require collagen or extracellular matrix remodelling. Additionally, relaxin has been implicated in the dilation of blood vessels' smooth muscle cells directly and through release of nitric oxide and atrial natriuretic peptide. Relaxin has also been used in the treatment of severe chronic pain, particularly pain arising from stretching, swelling, or dislocation of tissues.

DESCRIPTION OF THE SPECIFIC EMBODIMENTS

Figure 1E:
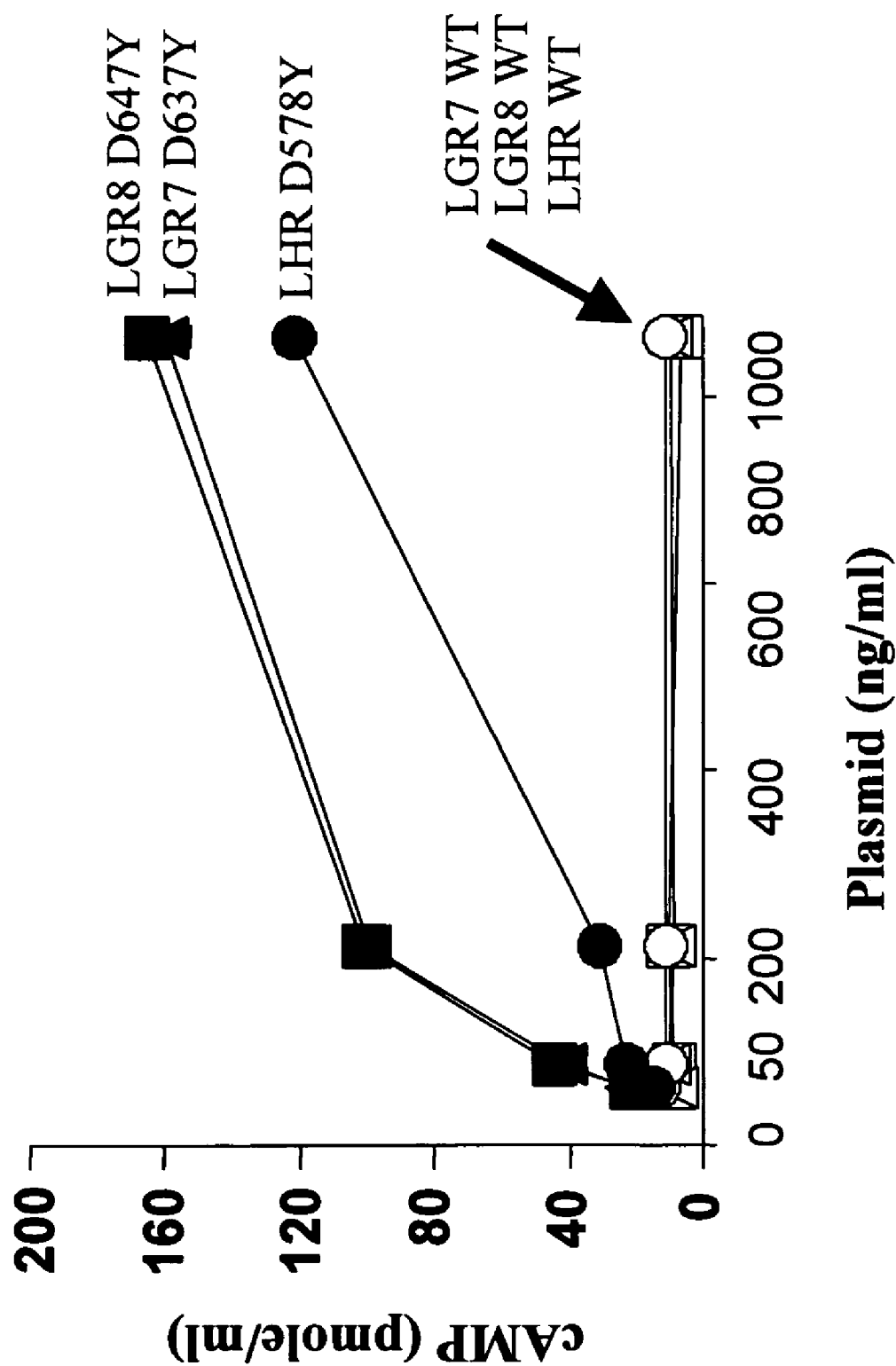
FIG. 1. Cloning of LGR8 and elucidation of its signaling mechanism. A) Sequence alignment of (SEQ ID NO:5) human LGR8 (Accession No. AF403384) with homologous receptors belong to the same subgroup of LGRs (SEQ ID NO:6) human LGR7, a snail LGR (SEQ ID NO:8) and a *Drosophila* LGR (SEQ ID NO:7). The sequence identity of human LGR8 was first deduced from high throughput genomic sequences using gene prediction programs GRAIL-1.3, FGENES-M, and NNPP located at BCM Launcher server, followed by subcloning using 5' and 3' RACE using gene-specific primers and Marathon-ready cDNA template (Clontech Inc., Palo Alto, Calif.) from human ovary, testis, pituitary, brain, and uterus. Amino acid numbers are on the right and the stop codon is marked with an asterisk. Putative N-glycosylation sites are circled. Identical residues are highlighted by a dark background. The N-terminal signal peptide for secretion in each polypeptide is underlined. The consensus LDL receptor cysteine-rich motifs are indicated by bold italics. Different structural motifs including the transmembrane (TM) region, intracellular loop (IL), and extracellular loop (EL), are indicated by arrowheads. Shaded residues are identical in the human LGR7 and snail LGR sequences. Residue numbers are shown on the right and gaps are included for optimal protein alignment. The BLOCK Maker program was used to align and generate the highly conserved ungapped blocks of the aligned LGR polypeptides from different species. B) Phylogenetic relatedness of diverse LGRs from mammals and invertebrates. Full-length amino acid sequences of 11 LGRs from mammals (LH, FSH, and TSH receptors plus LGR4 to LGR8), sea anemone, nematode, pond snail, and *Drosophila* were analyzed by the neighboring-joining method from the Block alignments using a routine in CLUSTALW. h: human; s: pond snail; Dm: *Drosophila melanogaster* analyzed using the Blocks program. These LGRs could be divided into three major branches; the first subgroup include the three classical human glycoprotein hormone receptors as well as LGRs from sea anemone, nematode, and *Drosophila*, the second group includes human LGR4-6 and *Drosophila* LGR2, whereas the third subgroup includes human LGR7-8 and *Drosophila* LGR3. C) A gain-of-function LGR8 mutant mediated constitutive cAMP production in transfected cells. Based on the gain-of-function point mutation (LHR D578Y) found in the LH receptor gene of patients with familial male-limited precocious puberty, LGR8 with a homologous point mutation in transmembrane VI (LGR8 D637G) was generated. After transfection of expression constructs encoding wild-type or mutant receptors into 293T cells, basal cAMP levels were monitored. Transfection of 293T cells with increasing concentrations (0-500 ng/well) of expression vectors encoding LGR8 D647Y, LGR7(1) D637Y and LH receptor D578Y led to increases in basal cAMP levels in transfected cells. In contrast, cAMP levels in cells transfected with wild-type (WT) receptors were negligible (n=3; mean±SE).

High affinity relaxin receptors, polypeptide compositions related thereto, as well as nucleotide compositions encoding the same, are provided. The subject polypeptide and/or nucleic acid compositions find use in a variety of different applications, including the identification of homologous or related genes; for the identification of endogenous ligands for these novel receptors; the production of compositions that modulate the expression or function of the receptors; for gene therapy; for mapping functional regions of the receptors; in studying associated physiological pathways; for in vivo prophylactic and therapeutic purposes; as immunogens for producing antibodies; in screening for biologically active agents; and the like.

Relaxin is a hormone with a number of important functions, which include the modulation of the reproductive physiology of human beings and other mammals, including, but not limited to, maintaining pregnancy, effecting parturition, and enhancing sperm motility as an aid in fertilization.

Relaxin has significant effects on connective tissue, as evidenced by its role in pregnancy, for example on the pubic symphysis and rearrangement of collagenous filaments effecting parturition; depressant effects on the myometrium; preparation of the endometrium for implantation; role in luteolysis; growth and differentiation of the mammary glands; enhancement of sperm motility; and augmentation of the ability of sperm to penetrate the human cervix. Relaxin has been implicated in the dilation of cardiac and blood vessels' smooth muscle cells, and has also been used in the treatment of severe chronic pain, particularly pain arising from stretching, swelling, or dislocation of tissues.

Human relaxin and its methods of preparation, including synthesis in recombinant cell culture, are known. Included within the scope of the term "relaxin" are human relaxins from recombinant or native sources as well as relaxin variants, such as amino acid sequence variants. The predominant species of human relaxin in the corpus luteum and serum is the H2 relaxin form with a truncated B chain, i.e., relaxin H2(B29 A24), wherein the four C-terminal amino acids of the B-chain are absent. Also included within the scope of the term "human relaxin" are other insertions, substitutions, or deletions of one or more amino acid residues, glycosylation variants, unglycosylated human relaxin, organic and inorganic salts, covalently modified derivatives of human relaxin, human preprorelaxin, and human prorelaxin.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Characterization of LGR7 and LRG8

LGR7 and LRG8 are mammalian high affinity relaxin receptors, which are of the G-protein coupled, seven transmembrane family of proteins, specifically the subfamily of G-protein coupled seven trans-membrane proteins that are characterized by the presence of extra-cellular leucine rich repeat regions. LRG8 is novel; LRG7 is described in co-pending patent application U.S. Ser. No. 09/647,067. These proteins have both a G-protein coupled seven trans-membrane region and a leucine rich repeat extra-cellular domain. Both of these receptors mediate the production of cAMP in response to binding of relaxin, which production is inhibited by the addition of anti-relaxin antibodies.

The human LGR7 gene encodes two splicing--variants (see Hsu et al. 2000), of 757 and 723 amino acids, respectively. These molecules may be referred to as LGR7(1) and LGR7(2), respectively, or generically as LGR7. LGR7 is expressed in multiple tissues, including testis, ovary, prostate, intestine and colon. Expression of LGR7 is cell type-specific in different rodent tissues. In the uterus, the expression of LGR7 is mainly in the endometrial and muscularis layers but minimal in stromal and interstitial cells, consistent with the utero-muscular modulating activity of relaxin. In the cervix, LGR7 was found in all muscularis layer. In contrast, negligible staining is found in the skeletal muscle.

The sequence of LGR8 is provided as SEQ ID NO:1, and encodes a polypeptide of 754 amino acids (SEQ ID NO:2). LGR8 is mainly expressed in the brain, kidney, muscle, testis, thyroid, uterus, bone marrow and peripheral blood cells. In addition to relaxin, LGR8 is a receptor for INSL3, an insulin-like protein related to relaxin (Adham et al. (1993) *J. Biol. Chem.* 268:26668-26672; Burkhardt et al. (1994) *Genomics* 20: 13-19). InsL3, is expressed exclusively in prenatal and postnatal Leydig cells. INSL3 has a role in the development of the male urogenital tract and in female fertility. Mutations in InsL3 are associated with cryptorchidism.

Soluble fragments of LGR7 and LGR8 are constructed by deletion of the transmembrane domain of the receptor. For example, a soluble form of LGR7 is made by truncating the protein to delete the transmembrane domain at L402. Gain of function mutations in LGR7(1); LGR7(2) and LGR8 are made by amino acid substitution, for example in the molecules LGR8 D647Y, and LGR7(1) D637Y. These mutated receptors show increased basal levels of activity.

LGR7 and LGR8 Polypeptides

For use in the subject methods, either of the native LGR7 or LGR8 forms, modifications thereof, or a combination of forms may be used. Polypeptides of interest include the complete mature protein, soluble fragments derived therefrom, relaxin-binding domains, mutations which may be a gain of function or loss of function mutation, and other derivatives and fragments thereof. A fragment of a LGR7 or LGR8 peptide may be selected to achieve a specific purpose, including solubility, isolation of specific domains and binding regions, and the like. Fragments will usually comprise at least about 10 amino acids of the provided amino acid sequences, and comprise 25, 50, 100 or up to the complete polypeptide sequence.

The sequence of the LGR7 or LGR8 polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example automated synthesizers by Applied Biosystems Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Compound Screening

The availability of purified LGR7 or LGR8 and other components in the signaling pathways, e.g. relaxin, InsL3, altered copies of these molecules, etc., allows in vitro reconstruction of the signaling pathway. Two or more of the components may be combined in vitro, and the behavior assessed in terms of production of cAMP; modification of protein components, e.g. connective tissues; ability of different protein components to bind to each other etc. The components may be modified by sequence deletion, substitution, etc. to determine the functional role of specific residues.

Drug screening may be performed using an in vitro model, a genetically altered cell or animal, or purified LGR7 or LGR8 protein. One can identify ligands or substrates that compete with, modulate or mimic the action of LGR7 or LGR8. Areas of investigation include the development of treatments for altering connective tissue, which may be in connection with pregnancy and birth, with disease states such as scleroderma and fibromyalgia, with the treatment of pain associated with distortions in connective tissue; with the treatment of cryptorchidism; the treatment of endometriosis; the relaxation of smooth muscle cells; and the like.

Drug screening identifies agents that mimic LGR7 or LGR8 activity, either as an antagonist or as an agonist. A wide variety of assays may be used for this purpose, including labeled in vitro protein-protein binding assays, electrophoretic mobility shift assays, immunoassays for protein binding, and the like. Knowledge of the 3-dimensional structure of LGR7 or LGR8, derived from crystallization of purified synthetic LGR7 or LGR8 protein, leads to the rational design of small drugs that specifically inhibit LGR7 or LGR8 activity.

The term "agent" as used herein describes any molecule, e.g. protein or pharmaceutical, with the capability of altering or mimicking the physiological function of LGR7 or LGR8. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Relaxin or analogs thereof may be useful in the screening assays, as competitors, controls, in structural studies of binding sites, etc. A number of such molecules have been described, for example, see U.S. Pat. Nos. 6,200,953; 5,326,694; 5,320,953; 5,179,195; 5,145,962; 5,053,488; 5,023,321; 4,871,670; 4,758,516; and 4,656,249.

The compounds having the desired pharmacological activity may be administered in a physiologically acceptable carrier to a host for treatment of connective tissue disorders, during pregnancy etc. The compounds may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-10 wt %.

Antibodies Specific for LGR7 or LGR8 Polypeptides

The present invention provides antibodies specific for LGR7 or LGR8 polypeptides, e.g. any one of the variants, polypeptides, or domains described above. Such antibodies are useful, for example, in methods of detecting the presence of LGR7 or LGR8 in a biological sample, and in methods of isolating LGR7 or LGR8 from a biological sample.

The LGR7 or LGR8 polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments-of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a LGR7 or LGR8 polypeptide, particularly a human LGR7 or LGR8 polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Uses of LGR7 or LGR8 Agonists and Antagonists

As receptors for relaxin and lnsL3, LGR7 and LGR8 have important roles in the physiology of pregnancy, reproductive development, other biological processes relating to smooth muscle and to connective tissue;-and the like. Formulations of LGR8 or LGR9, particularly the soluble receptor, as well as other agents that act as agonists or antagonists of these receptors find clinical use.

Agonists or other molecules that simulate the effect of relaxin affect epithelial cells, blood vessels, stromal cells (putative fibroblasts), and smooth muscle in the cervix and vagina, e.g. by promoting the onset of labor, increasing endometrial cells, inducing synthesis of mucins, regulating pituitary prolactin, oxytocin, and vasopressin release, etc.

These molecules also have important effects on the vascular system. Agonists, such as relaxin, are angiogenic in the endometrial lining, and plays a role in the attachment of the embryo to the uterus. They can be administered to increase blood flow and vasodilation of vascular beds. Methods for the use of relaxin to increase angiogenesis are described in U.S. Pat. No. 6,211,147. Relaxin and other agonists can act as a factor in protection against arteriosclerosis and ischemic or thrombotic pathologies, by inducing dilation of blood vessels' smooth muscle cells which results in an increment of blood flow; inhibits coagulation processes, intensifies the fibrinolysis and lowers blood concentration of lipids and sodium. This effect is mediated both directly, and through release NO and ANP, which largely contribute to the effect on vessel walls and blood components. See, for example, U.S. Pat. No. 5,952,296.

Agonists also act as an anti-fibrinolytic agent by decreasing collagen production, increasing collagen breakdown, and reducing the production of the collagenase inhibitor, TIMP Agonists may act directly on stromal cells to promote remodeling of the extracellular matrix.

Agonist-induced remodeling of connective tissue has potential for clinical applications, for example in the treatment of systemic sclerosis, or scleroderma, and as a cervical softening agent at term. Conversely, antagonists of LGR7 or LGR8 find use in the prevention of labor, for example to inhibit pre-term labor.

Agonists of LGR7 or LGR8 also find use in the treatment of fibromyalgia, and may also include the treatment of neurological disorders, for example Alzheimer's disease, Parkinson's, and/or other conditions such as ADD.

Another use of the LGR7 or LGR8 agonists is as an analgesic and palliative for intractable pain (see U.S. Pat. No. 5,656,592). Although relaxin and other agonists can be used generally as an analgesic and palliative for pain, the conditions most amenable to its therapeutic administration are those in which unusual stress is chronically placed on tissues because of an acquired or inherent malformation which results in the displacement of tissues from their natural disposition in the body. These agents finds utility, for example, in the treatment of severe chronic pain, particularly pain arising from stretching, swelling, or dislocation of tissues.

Agonists of LGR8 in particular find use in the treatment of cryptorchidism, a condition that is related to the ligand of LGR8, InsL3. The term cryptorchidism indicates a testis, which has failed to descend to the scrotum and is located at any point along the normal path of descent or at an ectopic site. Hormones play a pivotal role in testicular descent except during the migration to the level of internal inguinal ring. Cryptorchidism is present in about 4.5% of newborns with a higher incidence in preterms. The incidence decreases to 1.2% by the first year. It is classified as palpable and impalpable. The most common site of an ectopic testis is superficial inguinal pouch. Retractile testis is often bilateral and most common in boys between5 and 6 years of age. Hypospadias and inguinal hernias are the most common associated anomalies seen with undescended testis. Common complications include torsion and atrophy of testis. Infertility is seen in about 40% of unilateral and 70% of bilateral cryptorchidism. Undescended testis is 20 to 40 times more likely to undergo malignant transformation than normal testis.

Formulations

The compounds of this invention can be incorporated into a variety of formulations for therapeutic administration. Particularly, agents specifically bind to and activate LGR7 or LGR8; agents that block binding of native ligands, e.g. relaxin or InsL3, to LGR7 or LGR8; agents that modulate expression of LGR7 or LGR8; LGR7 or LGR8 polypeptides and analogs or fragments thereof; etc., are formulated for administration to patients for various clinical purposes, as previously described. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The agents may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the targeted site, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

LGR7 or LGR8 Nucleic Acids

The invention includes novel nucleic acids having a sequence set forth in SEQ ID NO:1; nucleic acids that hybridize under stringent conditions, particularly conditions of high stringency, to the sequence set forth in SEQ ID NO:1; genes corresponding to the provided nucleic acids; sequences encoding the polypeptide set forth in SEQ ID NO:2 (LGR8); and fragments and derivatives thereof.

The nucleic acids of the invention include nucleic acids having sequence similarity or sequence identity to SEQ ID NO:1. Nucleic acids-having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to SEQ ID NO:1 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

In one embodiment, hybridization is performed using at least 18 contiguous nucleotides (nt) of SEQ ID NO:1 or a DNA encoding the polypeptide of SEQ ID NO:2. Such a probe will preferentially hybridize with a nucleic acid comprising the complementary sequence, allowing the identification and retrieval of the nucleic acids that uniquely hybridize to the selected probe. Probes of more than 18 nt can be used, e.g., probes of from about 18 nt to about 25, 50, 100, 250, or 500 nt, but 18 nt usually represents sufficient sequence for unique identification.

Nucleic acids of the invention also include naturally occurring and synthetically produced variants of the nucleotide sequences (e.g., degenerate variants, gain of function mutations, soluble forms, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% bp mismatches, and can contain as little as even 5-15%, or 2-5%, or 1-2% bp mismatches, as well as a single bp mismatch.

The invention also encompasses homologs corresponding to the nucleic acids of SEQ ID NO:1 or a DNA encoding the polypeptide of SEQ ID NO:2, where the source of homologous genes can be any mammalian species, e.g., primate species, particularly human; rodents, such as rats; canines, felines, bovines, ovines, equines, fish, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul, et al. *Nucleic Acids Res.* (1997) 25:3389-3402.

The subject nucleic acids can be cDNAs or genomic DNAs, as well as fragments thereof, particularly fragments that encode a biologically active polypeptide and/or are useful in the methods disclosed herein (e.g., in diagnosis, as a unique identifier of a differentially expressed gene of interest, etc.) The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, to about 500 contiguous nt selected from the nucleic acid sequence as shown in SEQ ID NO: 1. For the most part, fragments will be of at least 18 nt, usually at least 25 nt, and up to at least about 50 contiguous nt in length or more.

Probes specific to the nucleic acid of the invention can be generated using the nucleic acid sequence disclosed in SEQ ID NO:1 or a DNA encoding the polypeptide of SEQ ID NO:2. The probes are preferably at least about 18 nt, 25 nt or more of the corresponding contiguous sequence. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of one of the provided sequences. More preferably, probes are designed based on a contiguous sequence of one of the subject nucleic acids that remain unmasked following application of a masking program for masking low complexity (e.g., BLASTX) to the sequence., i.e., one would select an unmasked region, as indicated by the nucleic acids outside the poly-n stretches of the masked sequence produced by the masking program.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Modulation of LGR7 or LGR8 Activity

The LGR7 or LGR8 genes, gene fragments, or the encoded protein or protein fragments are useful in gene therapy to treat conditions associated with LGR7 or LGR8 activity. Inhibition is achieved in a number of ways. Antisense or siRNA LGR7 or LGR8 sequences may be administered to inhibit expression. Competitive binding antagonists, for example, a polypeptide that mimics LGR7 or LGR8 binding may be used to inhibit activity. Other inhibitors are identified by screening for biological activity in an LGR7 or LGR8 based binding assay. Upregulating activity is also of interest, for example through the introduction of mutations have a gain of function mutation, through increasing expression levels, and through administering agents that bind to and activate LGR7 or LGR8.

Expression vectors may be used to introduce the LGR7 or LGR8 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or LGR7 or LGR8 peptide may be introduced into tissues or host cells by any number of routes, including viral infection, microinjection, or fusion of vesicles. Jet injection may also be used for intramuscular administration, as described by Furth et al. (1992) *Anal Biochem* 205:365-368. The DNA may be coated onto gold microparticles, and delivered intradermally by a particle bombardment device, or "gene gun" as described in the literature (see, for example, Tang et al. (1992) *Nature* 356:152-154), where gold microprojectiles are coated with the LGR7 or LGR8 or DNA, then bombarded into skin cells.

Antisense molecules can be used to down-regulate expression of LGR7 or LGR8 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of such molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14:840-844).

In addition to antisense, small interfering RNA (siRNA) duplexes can be used to inhibit expression of jeb genes. siRNA are double stranded RNA molecules of at least about 18 nucleotides, and may be up to the length of the complete mRNA. Preferred siRNA for use in mammalian cells are from about 18 to 30 nucleotides, preferably from about 21 to 22 nucleotides in length. For example, see Elbashir et al. (2001) *Nature* 411:494-498.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars, heterocyclic bases, morpholino derivatives, and the like.

Agents that block LGR7 or LGR8 activity provide a point of intervention in an important signaling pathway. Numerous agents are useful in reducing LGR7 or LGR8 activity, including agents that directly modulate LGR7 or LGR8 expression as described above, e.g. expression vectors, anti-sense specific for LGR7 or LGR8; and agents that act on the LGR7 or LGR8 protein, e.g. LGR7 or LGR8 specific antibodies and analogs thereof, small organic molecules that block LGR7 or LGR8 binding activity, etc.

Diagnostic Uses

Polynucleotide-based reagents derived from the sequence of LGR7 or LGR8, e.g. PCR primers, oligonucleotide or cDNA probes, as well as antibodies against LGR7 or LGR8s, are used to screen patient samples, e.g. biopsy-derived tissues, amniotic fluid samples, blood samples, etc., for increased expression of LGR7 or LGR8 mRNA or proteins. DNA-based reagents are also designed for evaluation of chromosomal loci implicated in certain diseases e.g. for use in loss-of-heterozygosity (LOH) studies, or design of primers based on LGR7 or LGR8 coding sequence. Of particular interest is the use of LGR8 for genetic studies related to the diagnosis of cryptorchidism, which is associated with the expression of lnsL3, and it's activation of LGR8.

The polynucleotides of the invention can be used to detect differences in expression levels between two samples. A difference between the protein levels, or the mRNA in the two tissues which are compared, for example, in molecular weight, amino acid or nucleotide sequence, or relative abundance, indicates a change in the gene, or a gene which regulates it, in the tissue or cell sample.

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in an LGR7 or LGR8 coding region or control regions is associated with disease. Disease associated polymorphisms may include deletion or truncation of the gene, mutations that alter expression level, that affect the binding activity of the protein, the G protein activity, etc.

Changes in the promoter or enhancer sequence that may affect expression levels of LGR7 or LGR8 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express LGR7 or LGR8 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. Molecular Cloning: A Laboratory Manual, CSH Press 1989, pp.14.2-14.33.

A detectable label may be included in an amplification reaction. Suitable labels include fluorochromes, e.g. fluorescein isothiocyanate (FITC), rhodamine, Texas Red, phycoerythrin, allophycocyanin,6-carboxyfluorescein(6-FAM),2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type LGR7 or LGR8 sequence. Hybridization with the variant sequence may also be used to determine its presence, by Southern blots, dot blots, etc. The hybridization pattern of a control and variant sequence to an array of oligonucleotide probes immobilized on an array, may also be used as a means of detecting the presence of-. variant sequences. Single strand conformational polymorphism (SSCP) analysis, denaturing gradient gel electrophoresis(DGGE), and heteroduplex analysis in gel matrices are used to detect conformational changes created by DNA sequence variation as alterations in electrophoretic mobility. Alternatively, where a polymorphism creates or destroys a recognition site for a restriction endonucleases, the sample is digested with that endonucleases, and the products size fractionated to determine whether the fragment was digested. Fractionation is performed by gel or capillary electrophoresis, particularly acrylamide or agarose gels.

Screening for mutations in LGR7 or LGR8s may be based on the functional or antigenic characteristics of the protein. Protein truncation assays are useful in detecting deletions that may affect the biological activity of the protein. Various immunoassays designed to detect polymorphisms in LGR7 or LGR8 proteins may be used in screening. Where many diverse genetic mutations lead to a particular disease phenotype, functional protein assays have proven to be effective screening tools. The activity of the encoded LGR7 or LGR8 protein in binding assays, etc., may be determined by comparison with the wild-type protein. Proteins may also be screened for the presence of post-translational modification of the LGR7 or LGR8 proteins, e.g. under pathological conditions, including proteolytic fragments, amidation, acetylation etc.

Antibodies specific for LGR7 or LGR8 may be used in staining or in immunoassays. Samples, as used herein, include biological fluids such as blood, amniotic fluid, and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal LGR7 or LGR8 in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

In some embodiments, the methods are adapted for use in vivo. In these embodiments, a detectably-labeled moiety, e.g., an antibody, which is specific for LGR7 or LGR8 is administered to an individual (e.g., by injection), and labeled cells are located using standard imaging techniques, including, but not limited to, magnetic resonance imaging, computed tomography scanning, and the like.

Diagnostic screening may also be performed for polymorphisms that are genetically linked to a disease predisposition, particularly through the use of microsatellite markers or single nucleotide polymorphisms. Frequently the microsatellite polymorphism itself -is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) *Genomics* 24:225-233; Ziegle et al. (1992) Genomics 14:1026-1031; Dib et al., supra.

The detection methods can be provided as part of a kit. Thus, the invention further provides kits for detecting the presence of an mRNA encoding LGR7 or LGR8, and/or a polypeptide encoded thereby, in a biological sample. Procedures using these kits can be performed by clinical laboratories, experimental laboratories, medical practitioners, or private individuals. The kits of the invention for detecting a polypeptide comprise a moiety that specifically binds the polypeptide, which may be a specific antibody. The kits of the invention for detecting a nucleic acid comprise a moiety that specifically hybridizes to such a nucleic acid. The kit may optionally provide additional components that are useful in the procedure, including, but not limited to, buffers, developing reagents, labels, reacting surfaces, means for detection, control samples, standards, instructions, and interpretive information.

Geneticallyaltered Cell Oranimal Models for LGR7 or LGR8 Function

The subject nucleic acids can be used to generate transgenic animals or site specific gene modifications in cell lines. Transgenic animals may be made through homologous recombination, where the normal LGR7 or LGR8 locus is altered. Alternatively, a nucleic acid construct. is randomly integrated into the genome. Vectors for stable integration include plasmids, retroviruses and other animal viruses, YACs, and the like.

The modified cells or animals are useful in the study of LGR7 or LGR8 function and regulation. For example, a series of small deletions and/or substitutions may be made in the LGR7 or LGR8 gene to determine the role of different residues in ligand binding, signal transduction, etc. Of interest are the use of LGR7 or LGR8 to construct transgenic animal models for pregnancy related disorders, connective tissue disorders, etc. where expression of LGR7 or LGR8 is specifically reduced or absent. Specific constructs of interest include anti-sense LGR7 or LGR8, which will block LGR7 or LGR8 expression and expression of dominant negative LGR7 or LGR8 mutations. A detectable marker, such as lac Z may be introduced into the LGR7 or LGR8 locus, where up-regulation of LGR7 or LGR8 expression will result in an easily detected change in phenotype.

One may also provide for expression of the LGR7 or LGR8 gene or variants thereof in cells or tissues where it is not normally expressed or at abnormal times of development. By providing expression of LGR7 or LGR8 protein in cells in which it is not normally produced, one can induce changes in cell behavior, e.g. in the control of endometriosis, alterations in connective tissue, and the like.

DNA constructs for homologous recombination will comprise at least a portion of the LGR7 or LGR8 gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185: 527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human -mammal, such as laboratory animals, domestic animals, etc. The transgenic animals may be used in functional studies, drug screening, etc., e.g. to determine the effect of a candidate drug on pregnancy and birth, etc.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy- with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Four orphan receptors, LGR4-7, have recently been isolated. These have structural features similar to those of the gonadotropin and thyrotropin receptors. Based on structural motifs and phylogenetic analysis, the orphan LGRs could be subdivided into two subgroups, with LGR4-6 as one group and LGR7 as another. Orthologous genes for each subgroup of LGR have been found in invertebrates. Similar to its snail and fly orthologs, human LGR7 has a unique N-terminal cysteine-rich LDL receptor-like domain preceding the multiple leucine-rich repeats found in the ectodomain of all other LGRs. Furthermore, constitutively active LGR7 mutants showing ligand-independent cAMP production were constructed based on gain-of-function point mutations found in the LH receptor of patients with male-limited precocious puberty.

A new human LGR is identified herein, which belongs to the same subgroup as LGR7 and is named LGR8 based on the chronological order of discovery. As shown in FIG. 1A, sequence analysis indicated LGR8 shared about 60% identity with LGR7 in both the ectodomain and the transmembrane region. Phylogenetic analysis showed that LGR8 has the closest relatedness with LGR7 and a *Drosophila* orthologous receptor as compared to other human LGRs (FIG. 1B). Similar to the gain-of-function mutants identified for LGR7, a LGR8 mutant with a D578G substitution in the transmembrane VI of this receptor conferred ligand-independent increases in basal cAMP production in transfected cells (FIG. 1C). These findings suggested that LGR8, like LGR7, could couple with the Gs protein to activate adenylate cyclase.

Although both LGR7 and LGR8 are orphan receptors, the similar cryptorchidism phenotypes of lnsL3 null mice and mutant mice with a disruption of the mouse GREAT gene (an LGR8 ortholog) led to the hypothesis that the relaxin family of peptide proteins are the ligands for LGR7 and LGR8. This hypothesis was reinforced by earlier reports showing relaxin stimulation of cAMP production in endometrial, anterior pituitary and other cells.

Figure 2A:
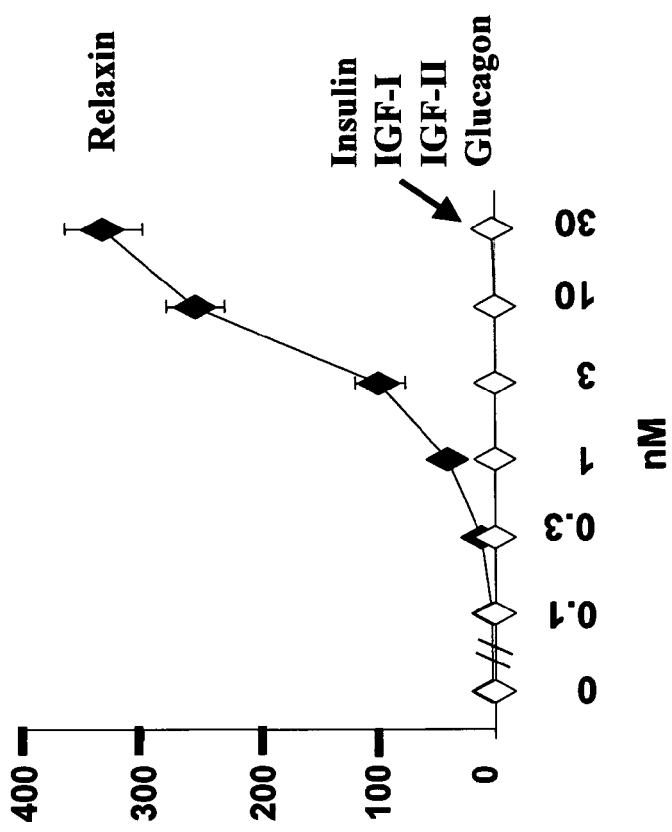
FIG. 2. LGR7 and LGR8 are relaxin receptors. Porcine relaxin stimulated cAMP production by 293T cells expressing recombinant LGR7 (A) and LGR8 (B). Relaxin, but not insulin, IGF-1, or IGF-11 does-dependently increased the cAMP production by 293T cells overexpressing recombinant receptors. In addition, glucagon, a Gs-coupled receptor activator, also has no effect on cAMP production by LGR7 and LGR8. Although there are two splicing variants for human LGR7 (Hsu et al. (2000) *Mol Endocrinol*. 14(8):1257-71), the long form was used exclusively for the present analysis.

293T cells expressing human LGR7 or LGR8 were treated with porcine relaxin. As shown in FIG. 2A and B, relaxin treatment resulted in dose-dependent increases in cAMP production with an $EC_{50}$ of 0.1 and 0.5 nM for LGR7 and LGR8, respectively. In contrast, treatment with structural homologs, insulin, IGF-I, and IGF-II, as well as an unrelated peptide hormone glucagon was ineffective. The present findings demonstrate that relaxin is the cognate ligand for two G protein-coupled receptors, LGR7 and LGR8, capable of activating adenylate cyclases.

Figure 3A:
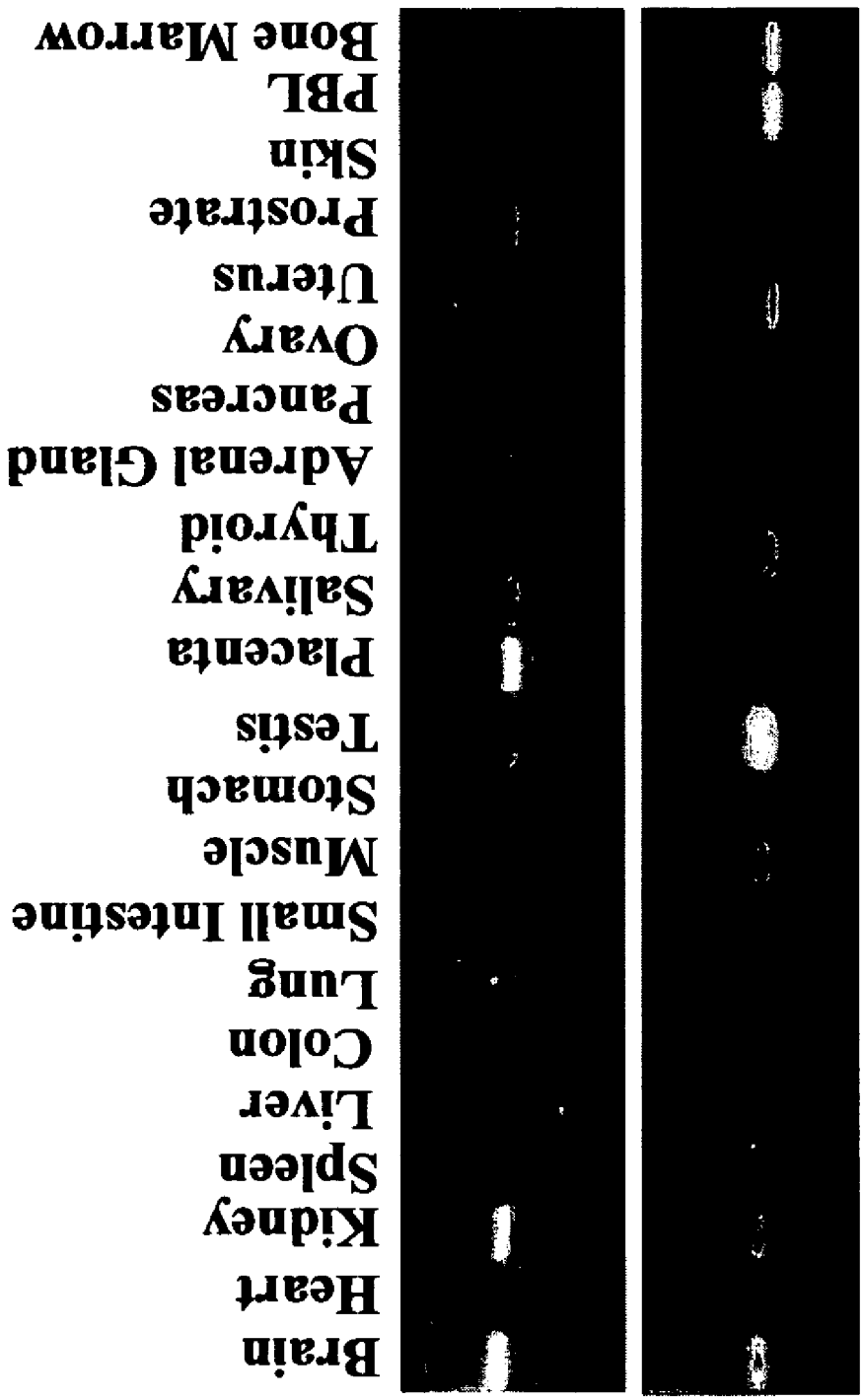
FIG. 3. Tissue distribution of LGR7 and LGR8. A) Profiles of LGR7 and LGR8 transcripts in human tissues. PCR analyses of LGR7 and LGR8 in diverse human tissues were conducted using human cDNA from ovary, testis, kidney, thyroid, spleen, brain, pancreas, pituitary, uterus, prostate, heart, hypothalamus, placenta, and lymph nodes (1 ug/reaction) and LGR gene-specific primer pairs under high-stringency conditions. Specific bands are indicated by arrowheads. PCR amplification was carried out under high stringency conditions to minimize nonspecific signals (denaturation: 94C, 30 sec, annealing and extension: 68-72C, 3 min; 35 cycles). B) Immunohistochemical analysis of LGR7 expression in rodent reproductive tracts. Specific LGR7 staining in uterus, cervix, mammary gland, and pituitary were indicated by black arrowheads. Epithelial layer (EL); stromal layer (SL); Muscularis layer (ML); mammary gland and nipple, anterior pituitary, intestine, skin, etc. Staining using control antiserum showed negligible signals.
Figure 3B:
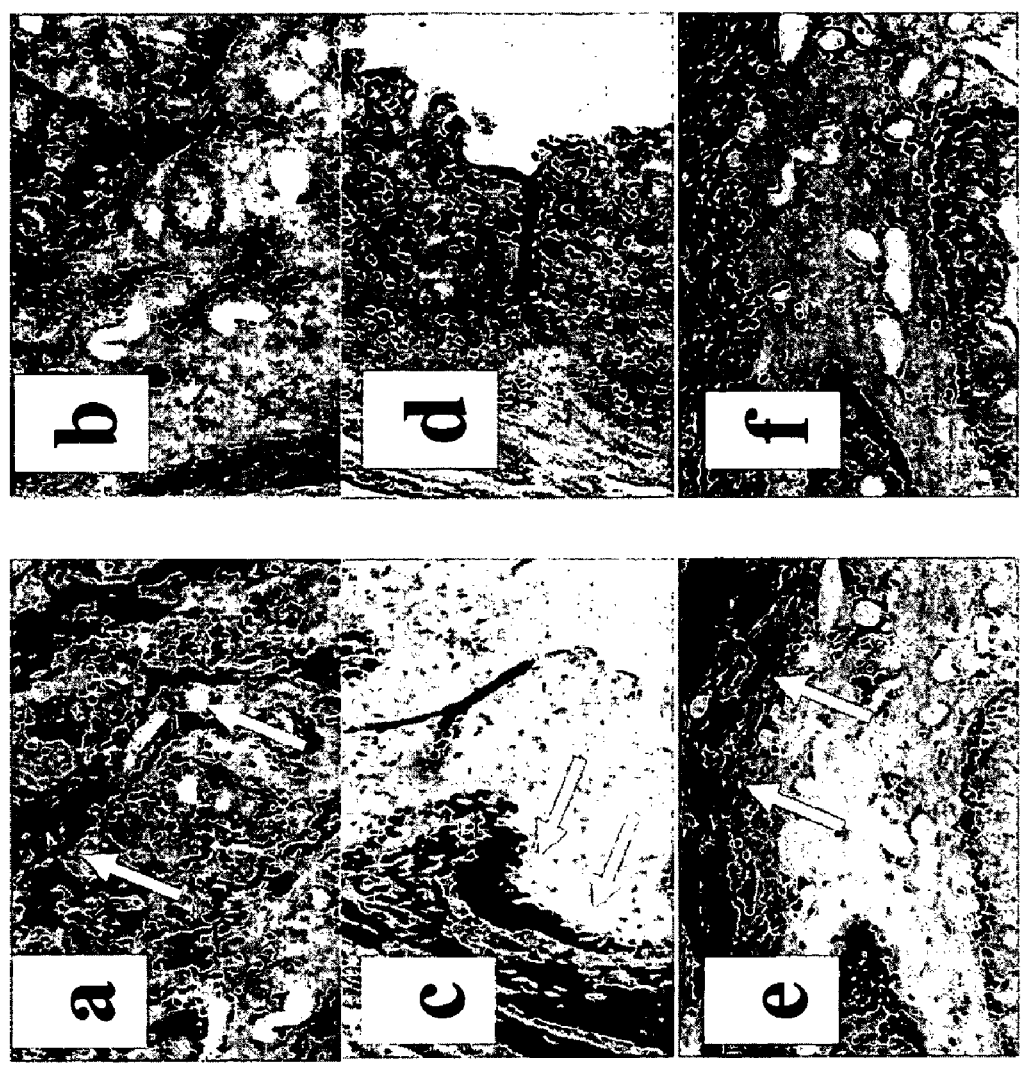

To determine whether the expression of LGR7 and LGR8 is consistent with previous studies on relaxin target sites, the expression pattern of LGR7 and LGR8 was determined in diverse human tissues (FIG. 3A). Reverse transcription-PCR analysis using a panel of 23 different human cDNAs indicated that LGR7 is expressed in diverse tissues as demonstrated previously using Northern blotting analysis, whereas LGR8 is mainly present in the brain, kidney, muscle, testis, thyroid, uterus, bone marrow and peripheral blood cells. Specific antibodies were generated against the ectodomain of LGR7. Immunohistochemical analysis demonstrated that the expression of LGR7 is cell type-specific in different rodent tissues. In the uterus, the expression of LGR7 is mainly in the endometrial and muscularis layers but minimal in stromal and interstitial cells, consistent with the utero-muscular modulating activity of relaxin. In the cervix, LGR7 was found in all muscularis layer. In contrast, negligible staining was found in the skeletal muscle (FIG. 3B).

Figure 4B:
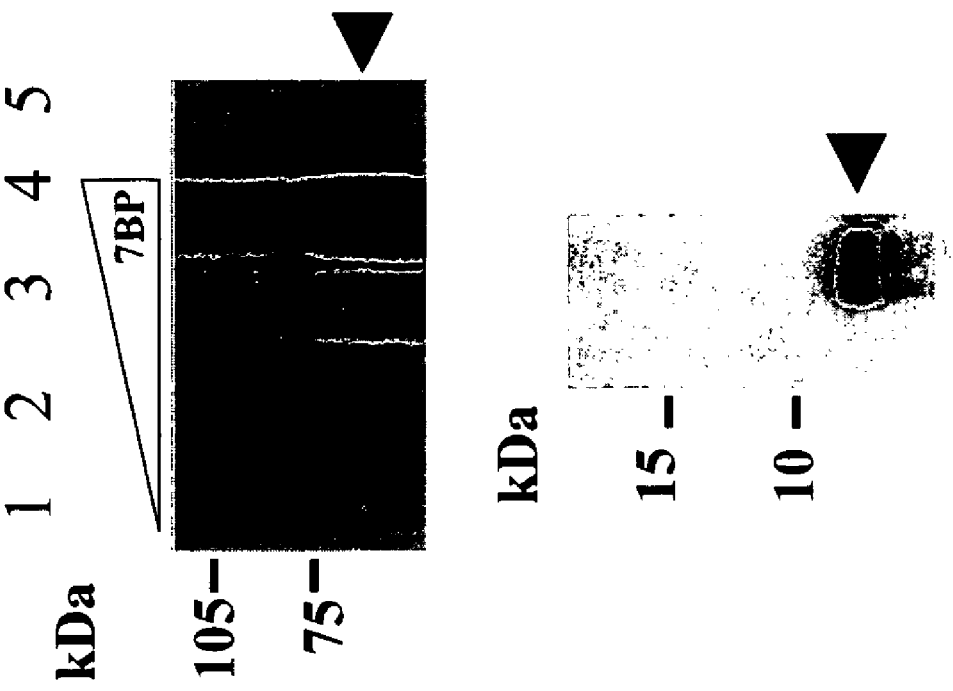
FIG. 4. Neutralization of relaxin actions using the ligand binding domain of LGR7. A) Generation of the soluble ectodomain of LGR7 (7BP) using an anchored receptor approach. Permanent 293T cell lines overexpressing 7BP-CD8 were cultured under serum-free conditioned and treated with thrombin for three days, and soluble recombinant 7BP tagged with 6-His and M1 epitopes was purified using Nickel and anti-FLAG affinity chromatography under natural conditions. Specific 7BP bands following Western blotting analysis using M1-FLAG antibody was indicated by an arrowhead (lane B). Homologous domain of LGR4 (4BP) was also generated using the same approach and shown on lane C. B) Specific interaction of relaxin and 7BP. Purified porcine relaxin was incubated with recombinant 7BP in PBS and crosslinked with disuccinimidyl suberat, before boiling for 5 min. under denaturing conditions and resolved in 7.5% SDS PAGE. The relaxin/7BP complex was detected by an anti-relaxin antibody whereas 4BP showed negligible interaction with relaxin. C) Recombinant 7BP blocked the stimulatory effects of relaxin on LGR7 and LGR8. 293T cells expressing LGR7 or LGR8 were treated with 0.1 nM relaxin in combination with different dosage of 7BP or 4BP for 24 h under serum-free conditions. D) Treatment of cultured rat myometrial cells with 7BP blocked the relaxin stimulation of cAMP production. Uterine tissues were obtained from 25-day-old female rats implanted with diethystibestrol for 3 days. Myometrial cells were prepared by serial digestions with trypsin and collegenase and cultured. Cells were treated with 1 nM of porcine relaxin with or without recombinant 7BP under serum-free conditions for 24 h.
Figure 4A:
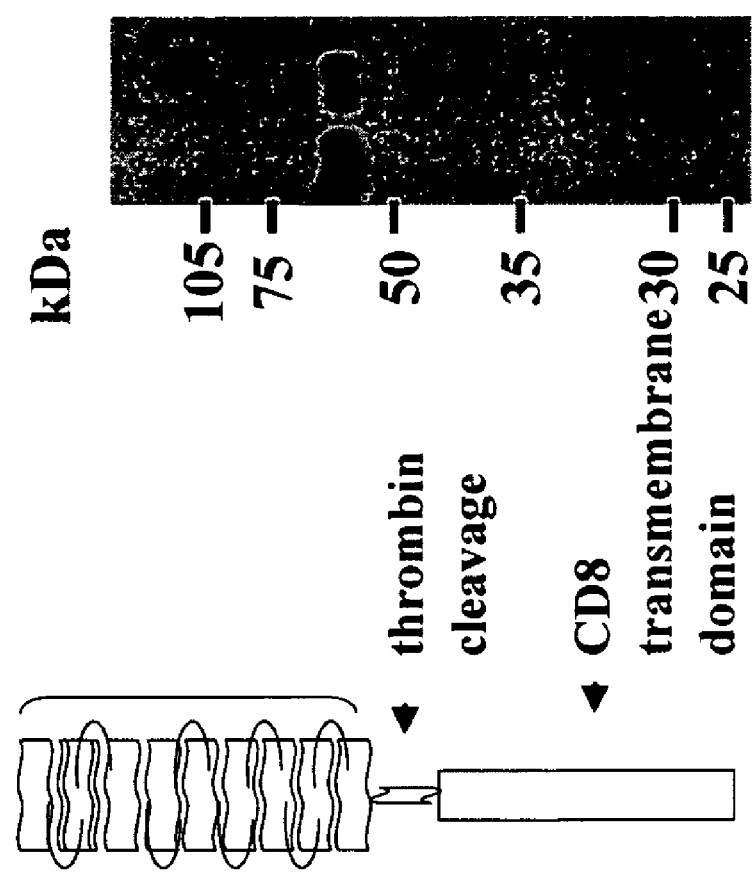

Studies on the classical LGRs have demonstrated that the ectodomains of gonadotropin and thyrotropin receptors are the ligand-binding regions and an anchored receptor approach was previously used to derive the soluble ectodomains of these receptors as functional antagonists. Using this strategy, permanent cell lines expressing the ectodomain of LGR7 fused to the single transmembrane region of CD8 through a thrombin cleavage site were isolated (FIG. 4A). Following thrombin treatment, mg quantities of the soluble ectodomain of LGR7, named as 7BP, was generated. As shown in FIG. 4B, cross-linking analysis demonstrated a concentration-dependent formation of complexes between relaxin and 7BP whereas a homologous soluble ectodomain from rat LGR4 (4BP) showed negligible interaction with relaxin. In addition, co-treatment with 7BP dose-dependently blocked the stimulatory effects of relaxin to activate LGR7 and LGR8 expressed in293T cells (FIG. 4C), but co-treatment with 4BP was ineffective. Consistent with an earlier finding, treatment with relaxin stimulated cAMP production by cultured rat myometrial cells (FIG. 4D). This stimulatory effect of relaxin was also antagonized by co-treatment with 7BP.

Furthermore, subcutaneous administration of 7BP (500 µg/day) for 4 days between post-conception days 17 and 20 in pregnant mice led to parturition delay and nipple malformation (Table 1).

TABLE 1

Delay of Parturition and Inhibition of Nipple Development by 7BP

|  | Control | 7BP treatment |
|---|---|---|
| Pregnancy Duration (hours) | 508.8 ± 8.9 | 532.2 ± 9.0 |
| Nipple size (length × width, mm$^2$) | 1.55 ± 0.1 | 1.01 ± 0.06 |

Prolonged duration of straining was found. There were lower incidences of normal maternal behavior observed at birth. In addition, little or no milk was observed in the abdomen of most live pups of 7BP-treated mice, whereas abundant milk was observed in the abdomen of all live pups of control mice. The inability of 7BP-treated mother to nurse the young is consistent with findings in relaxin null mice. Although earlier studies have used neutralizing antibodies to relaxin to delay parturition in pregnant rats, a more pronounced antagonistic effect of 7BP was observed here, suggesting that other endogenous ligands for LGR7, in addition to relaxin, could be important in the parturition process.

The present identification of two orphan. G protein-coupled receptors as relaxin. receptors is in direct contrast to the well-known signaling mechanism of insulin and IGFs mediated by the tetrameric tyrosine kinase receptors. Although relaxin has been traditionally classified in the insulin family of hormones based on similar domain arrangements, the present results indicated that relaxin and related ligands could have diverged from insulin/IGF ligands before separation of the arthropods because an ortholog of LGR7 and LGR8 could be found in the fly genome (FIG. 1C) in addition to receptors homologous to the other two subgroups of mammalian LGRs (9).

The insulin ligand-signaling receptor system has been found to be important in nutrition, longevity, and reproduction in the *C. elegans*. It is likely that a subgroup of relaxin-related ligands evolved early to subserve tissue remodeling functions including actions on reproductive tracts in modern mammals. Indeed, a relaxin-like gene has been found in the primitive tunicates whereas a putative insulin-like protein in *Drosophila* exhibited greater sequence homology to mammalian relaxin than to insulin and IGFs. The proposed evolution of divergent receptor mechanisms for relaxin and insulin are consistent with their crystal structure analyses. Although relaxin, like insulin, crystallizes as a dimer, the orientation of the molecules in the respective dimers is completely different. Because the dimer interface determinants proposed for receptor binding for insulin and relaxin are quite different, it was proposed that these two structurally related hormones have evolved somewhat dissimilar mechanisms for receptor binding.

The identification of cAMP as a second messenger for relaxin is consistent with earlier findings of relaxin stimulation of cAMP production by human endometrial and rat pituitary cells as well as mouse pubic symphysis and rat cervical fragments. Unlike insulin, relaxin gene sequences are highly variable among different vertebrate species studied. The present availability of recombinant human LGR7 and LGR8 can provide uniform and convenient in vitro bioassays for relaxin, whereas the derivation of the soluble ligand-binding ectodomains can serve as functional antagonists for relaxin during tissue remodeling processes and pregnancy in human and lower species.

Figure 2B:
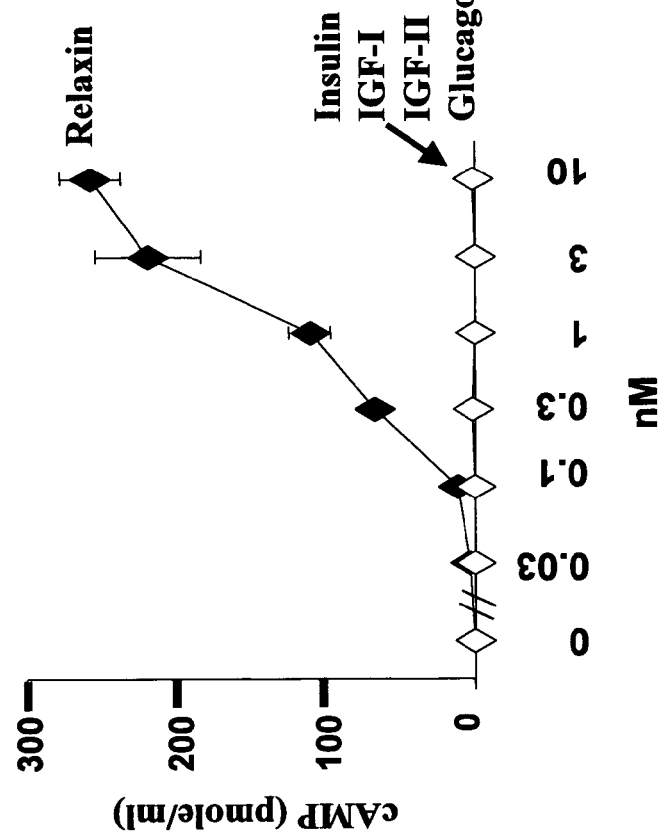

Although relaxin activates both LGR7 and LGR8 based on studies of recombinant receptors (FIG. 2), LGR7 is likely to mediate both endocrine and paracrine actions of relaxin whereas LGR8 is more important for a paracrine role, based on the observed lower sensitivity of LGR8 to relaxin. The existence of two relaxin receptors with overlapping tissue expression patterns raises issues regarding their respective physiological roles. LGR7 is expressed in tissues known to possess relaxin binding sites, including ovary, testis, uterus, brain, and heart. Because LGR7 transcript was also found in many tissues not previously known to be relaxin targets, it is interesting to analyze the potential action of relaxin in these tissues. In contrast, the expression of LGR8 is more restricted.

Although antepartum increases in circulating relaxin has been found in rat and selected species, relaxin may be a paracrine hormone in humans and is secreted by corpus luteum, placenta, and uterus to subserve local functions. The differential expression of LGR7 and LGR8 and the possible involvement of additional ligands for these receptors provide the basis to elucidate the role of these receptors and their ligands during pregnant states. Identification of LGR7 and LGR8 as relaxin receptors provides the basis to elucidate the differential ligand specificity and tissue distribution of these two proteins for the understanding of the diverse actions of relaxin during pregnant and nonpregnant states.

Preterm labor and delivery remain a major cause of perinatal morbidity, mortality, and long-term adverse neurodevelopmental outcome, whereas prolonged labor is also associated with major stress for mothers and infants. Although conflicting outcome has been reported for the use of relaxin as a labor-inducing agent, future studies on the signal transduction mechanism of relaxin receptors will allow the design of agonistic or antagonistic relaxin analogs for the treatment of disorders of labor onset. Elucidation of the ligand signaling mechanisms of relaxin receptors will also lead to a better understanding of the role of relaxin and related hormones in uterine and mammary growth. In addition to actions on reproductive tissues, relaxin has been shown to regulate pituitary prolactin, oxytocin, and vasopressin release, probably by binding to putative receptors in brain and pituitary. In addition, relaxin binding sites have been found in mast cells, and a human monocytic cell line.

Relaxin has important effects on the vascular system. It is angiogenic in the endometrial lining and plays a role in the attachment of the embryo to the uterus, and structural remodeling of the abdomen, joints and tendons to accommodate the growing fetus. In addition, relaxin regulates the circulatory system to ensure adequate blood flow and oxygenation to the growing fetus. It stimulates vasodilation of vascular beds by activating the endothelin B receptor subtype and inhibiting the vasoconstrictive effects of angiotensin II. Relaxin also acts as an anti-fibrinolytic agent by decreasing collagen production, increasing collagen breakdown, and reducing the production of the collagenase inhibitor, TIMP. Understanding of the vascular activities of relaxin mediated by its receptors will allow stimulation of new blood vessel growth in selective target tissues and ischemic wound sites.

Studies on this relaxin receptor will facilitate understandings on connective tissue remodeling and allow new treatments of skin conditions such as scleroderma. Although the major biological effect of relaxin is to remodel the mammalian reproductive tract and breast in pregnant females to facilitate the birth process and nursing, high levels of relaxin secreted by the prostate has also been found in human seminal plasma and might play a role in sperm motility and fertilization capacity. The present elucidation of relaxin receptors could facilitate the understanding of the role of relaxin in males.

The present study underscored the value of a genomic approach in the matching of orphan ligand-receptor pairs. Although relaxin has domain arrangements similar to those of the insulin/IGF family of proteins known to activate tetrameric tyrosine kinase receptors, the completely sequenced human genome has only one orphan insulin receptor-like gene that is unlikely to be the receptor for the divergent relaxin-like factors. Likewise, the analysis of paralogs of glycoprotein hormone subunit genes indicated that the limited number of remaining candidate ligands is unlikely to interact with orphan LGRs. Thus, the orphan LGRs are likely to interact with ligands other than the heterodimeric gonadotropins and thyrotropin.

The present demonstration of LGR7 and LGR8 as relaxin receptors indicated that a separate ligand signaling system has evolved for the relaxin subfamily of insulin-like genes, including lnsL3 and relaxin. Similar to the ancient origin of the insulin ligand/receptor system, structural orthologs for LGR7 and LGR8 could be traced to fly and snail, and phylogenetic analysis indicated that this subgroup of LGRs evolved before the emergence of Bilateria. Thus, the usage of two distinct receptor-signaling mechanisms for structurally-related insulin and relaxin family of peptide ligands is likely to be ancient in origin. It is becoming clear that the actions of relaxin and its related ligands (e.g. InsL3) are mediated by at least two related LGRs (7 and 8). Based on the hypothesized coevolution of the relaxin family of ligands and the orphan LGRs, future studies on the matching of InsL3 and related relaxin-like ligands (InsL4, RIF1, and RIF2) with LGR8 and the remaining orphan LGRs (LGR4-6) are of interest.

EXAMPLE 2

INSL3, also known as Leydig insulin-like peptide or relaxin-like factor, is a relaxin family member expressed in testis Leydig cells and ovarian theca and luteal cells. Male mice mutant for INSL3 exhibit cryptorchidism or defects in testis descent due to abnormal gubernaculum development whereas overexpression of INSL3 induces ovary descent in transgenic females. Because transgenic mice missing the LGR8 gene are also cryptorchid, INSL3 was tested as the ligand for LGR8. Here, it is shown that treatment with INSL3 stimulated cAMP production in cells expressing recombinant LGR8, but not LGR7. In addition, interactions between INSL3 and LGR8 were demonstrated following ligand receptor cross-linking. Northern blot analysis indicated that the LGR8 transcripts are expressed in gubernaculum whereas treatment of cultured gubernacular cells with INSL3 stimulated cAMP production and thymidine incorporation. Demonstration of INSL3 as the ligand for LGR8 facilitates understanding of the mechanism of testis descent and allows studies on the role of INSL3 in gonadal and other physiological processes.

Experimental Procedures:

Ovine and rat INSL3 were chemically synthesized and characterized as previously described. Human INSL3 and biotinylated ovine INSL3 were prepared similarly with the ovine INSL3 containing a single biotin molecule on the N-terminus of the A chain. The National Hormone and Pituitary Program (NIDDK, National Institutes of Health, Bethesda, Md.) supplied porcine relaxin. $^{125}$I-Streptavidin and streptavidin conjugated to horseradish peroxidase (HRP) were purchased from Amersham Biosciences, Inc (Piscataway, N.J.), whereas foskolin, glucagon, collagenase and trypsin were from Sigma Chemical Co. (St. Louis, Mo.). Sprague-Dawley rats were obtained from Simonsen Laboratories (Gilroy, Calif.). Animals were anesthetized and killed using $CO_2$. Animal care was consistent with institutional and NIH guidelines.

Human 293T cells were maintained in Dulbecco's modified Eagle's medium/Ham's F-12 (DMEM/F12) supplemented with 10% fetal bovine serum (FBS), 100 μg/ml penicillin, 100 μg/ml streptomycin, and 2 mM L-glutamine. When 70-80% confluent, cells were transfected with 10 μg of plasmid using the calcium phosphate precipitation method. After 18-24 h of incubation, media were replaced with DMEM/F12 containing 10% FBS. Forty-eight hours after transfection, cells ($10^5$/ml) were preincubated at 37° C. for 30 min in the presence of 0.25 mM 3-isobutyl-1-methyl xanthine (IBMX, Sigma Chemical Co.) before treatment with or without hormones for 12 h. Total cAMP content was measured in triplicate by a specific radioimmunoassay. All experiments were repeated at least four times using cells from independent transfections.

To estimate INSL3 binding, transfected cells were washed twice with D-PBS and collected in D-PBS before centrifugation at 400×g for 5 min. Cells pellets were resuspended in D-PBS containing 1 mg/ml BSA and incubated with increasing doses of the rat INSL3 at 4° C. for 24 h in the presence of biotinylated INSL3 (5 nM/tube). After incubation, cells were centrifuged and washed twice with 1% BSA/PBS before incubation with $^{125}$I-Streptavidin (400,000 cpm/tube) for 1 h at 4° C. After washing the cells three times, radioactivity in the pellets was determined. For protein blotting, transfected cells were incubated with biotinylated INSL3 (50 nM/tube) with or without an excess of rat INSL3 (1 μM/tube). After washing, pellets were incubated in D-PBS with disuccinimidyl suberate (0.5 mM) for 30 min. at room temperature. The cross-linked INSL3-LGR8 complexes were solubilized with 100 μl 1% Triton X-100 in 50 mM Tris-HCl. The lysates were denatured with SDS and 2-beta-mercaptoethanol, and fractionated using SDS-PAGE. After blotting onto nitrocellulose membranes (Hybond-P, Amersham) and blocking with a 5% milk solution, the blots were incubated for 2 h at room temperature with streptavidin (1:10,000 dilution) before development using enhanced chemiluminescence solution (ECL, Amersham Life Science). In addition, epitope-tagged LGR8 was extracted with 1% Triton X-100 from cells transfected with the LGR8 expression plasmid and incubated with the M1 antibody for 1 h. Protein G-Sepharose was subsequently added to precipitate the M1-tagged receptor protein. The precipitate was further fractionated using SDS-PAGE followed by immunoblotting using the M1 antibody.

Total RNA from different rat tissues were extracted using the RNeasy purification kits (QIAGEN Inc. Chatsworth, Calif.) before Northern blotting. Rat orthologs for LGR7 and LGR8 were identified in the GenBank (accession number AC098607 and AC098990, respectively). These sequences were used in reverse transcription-PCR to yield LGR8 and LGR7 probes of 230 and 226 bp, respectively.

Gubernacular cells were isolated by modifying an earlier method. Tissues were removed from one-week-old rats and cut into 1 mm pieces, and dissociated for 2 h at 37° C. in DMEM/F12 with 0.1% collagenase. Cell debris was removed by passage through a sterile filter and cells were collected by centrifugation. After suspension in DMEM/F12 with 10% FBS, 100 μg/ml penicillin, 100 μg/ml streptomycin, and 2 mM L-glutamine, cells were cultured for 24 h in 5% $CO_2$ incubator at 37° C. The cells were then washed once with serum-free medium and treated in DMEM/F12 containing IBMX with or without hormones and reagents. After 16 h of incubation, total cAMP was measured in triplicates as described above. For thymidine incorporation studies, gubernacular cells ($2 \times 10^5$ cells/500 μl) were cultured in 5 ml polypropylene Falcon tubes (Becton Dickinson, Franklin Lakes, N.J.) with or without hormones together with 1 μCi/tube of [methyl-$^3$H]thymidine (Amersham Pharmacia Biotech). After 24 h of culture, cells were washed once and resuspended with ice-cold PBS before centrifugation at 2000×g for 30 min. at 4° C. Radioactivities in the washed cell samples were determined using a β-photomultiplier.

Results

Figure 5:
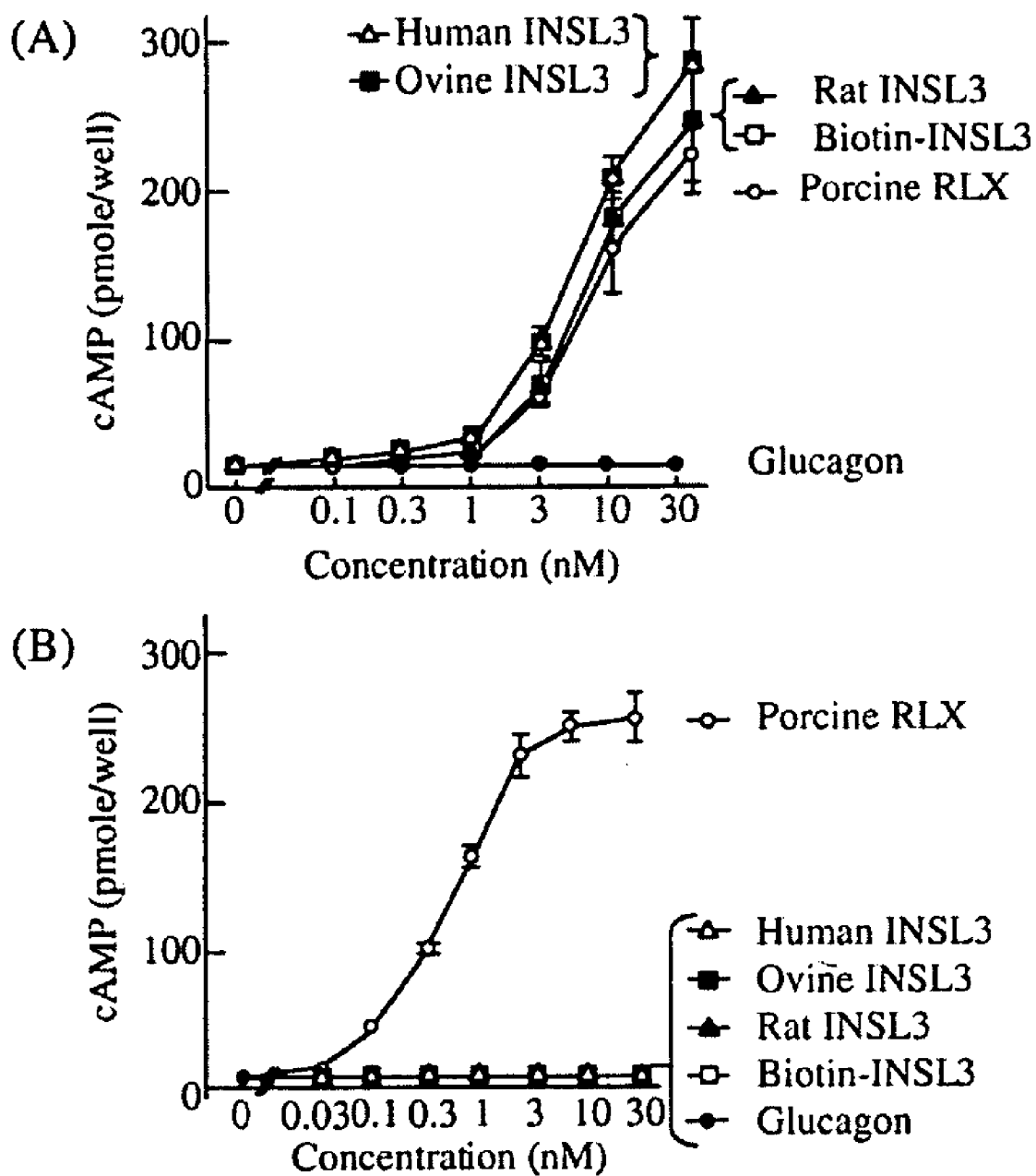
FIG. 5. Activation of LGR8 but not LGR7 by INSL3. Cells expressing recombinant human LGR8 or LGR7 were treated with INSL3 from different species, or with biotinylated-ovine INSL3 (Biotin-INSL3), porcine relaxin (RLX) or glucagon. Ligand signaling was estimated based on extracellular cAMP production. A) LGR8. B) LGR7.

INSL3 is the cognate ligand for LGR8. Although INSL3 binds to gubernacular homogenates, and induces growth of rat gubernaculum in organ cultures, the exact nature of the INSL3 receptor is unknown. Human fetal kidney 293T cells were transfected with expression vectors encoding human LGR8 or the related LGR7 for testing of INSL3 signaling. In cells expressing LGR8 (FIG. 5A), treatment with synthetic human, ovine, or rat INSL3 led to dose-dependent increases in cAMP production. Although treatment with biotinylated-ovine INSL3 or porcine relaxin (RLX) was also effective, treatment with glucagon did not increase cAMP production. In contrast, cells expressing LGR7 responded only to relaxin treatment whereas treatments with INSL3 from different species or human glucagon were ineffective (FIG. 5B). These results indicated that INSL3 is a specific ligand for LGR8.

Figure 6A:
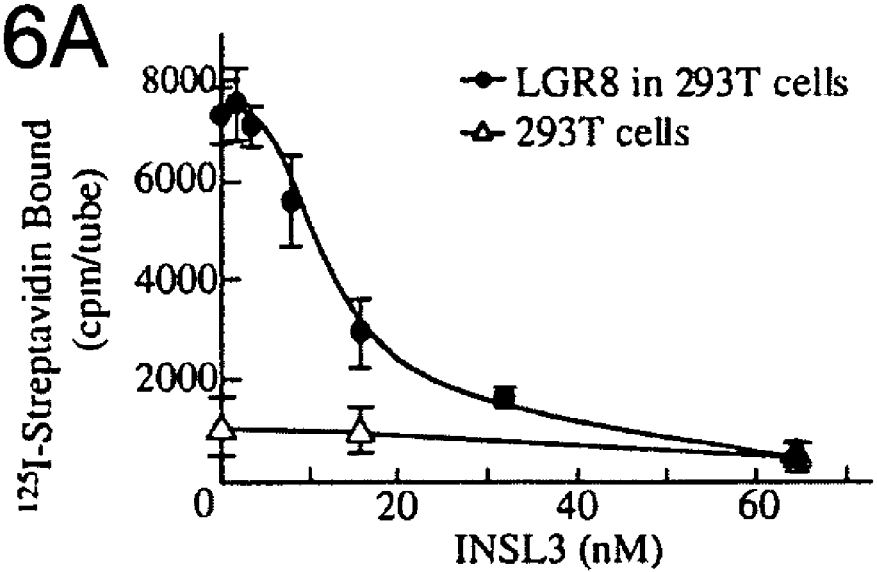
FIG. 6. Direct binding of biotinylated INSL3 to LGR8. A) Ligand binding assays. Cells expressing LGR8 were incubated with 5 nM of biotinylated ovine INSL3 with or without increasing levels of rat INSL3. Specific INSL3 binding to LGR8 was estimated using labeled strepavidin. B) Cross-linking of INSL3 to LGR8. Cells expressing LGR8 were incubated with biotinylated INSL3 (Biotin-INSL3) with or without a 20-fold excess INSL3 before cross-linking. Complexes of biotinylated INSL3 and LGR8 were detected using the avidin-HRP following SDS-PAGE and protein blotting. Lane 1, biotin-INSL3 alone; lane 2, INSL3-LGR8 complexes; lane 3; competition with excess non-biotinylated INSL3; lane 4, recombinant LGR8 detected using the M1 antibody.
Figure 6B:
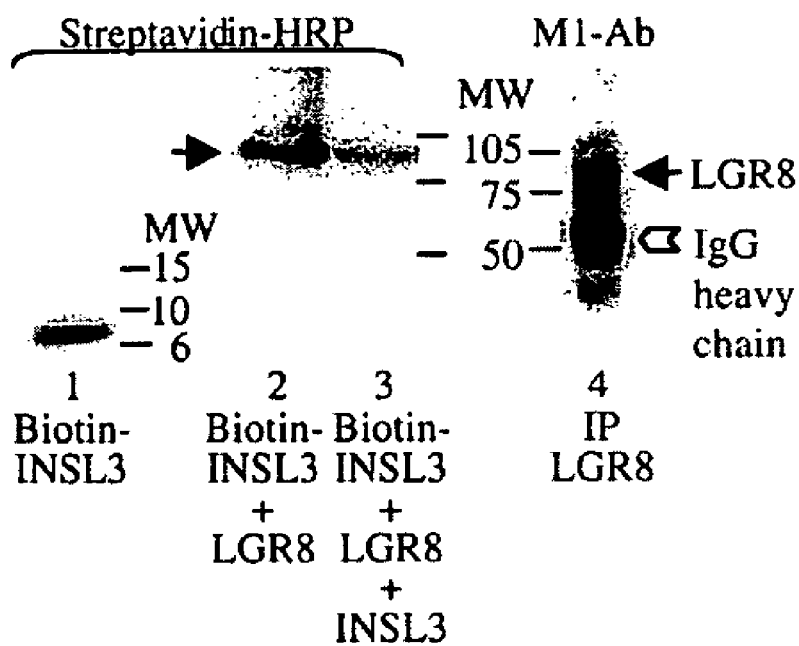

To demonstrate the direct binding of INSL3 to LGR8, cells expressing LOR8 were incubated with biotinylated INSL3 with or without increasing doses of non-biotinylated INSL3. Following incubation at 4 C for 24 h, cells were washed and incubated further with $I^{125}$-labeled streptavidin to estimate the levels of cell-bound biotinylated INSL3. As shown in FIG. 6A, specific binding of biotinylated INSL3 to LGR8 could be competed by non-biotinylated INSL3 in a dose-dependent manner with an $ED_{50}$ of 12 nM (filled circles). In contrast, 293T cells without LGR8 expression did not exhibit specific binding (open triangles). The formation of the LGR8-INSL3 complexes was further estimated following cross-linking and protein blotting before signal detection using avidin-horseradish peroxidase (HRP). As shown in FIG. 6B, biotinylated INSL3 cross-linked with LGR8 could be detected as a high MW band (~84 KDa) whereas a 20-fold excess of non-biotinylated INSL3 decreased signal intensity (lanes 2 and 3). In contrast, the free biotinylated INSL3 migrated at 6.5 KDa (FIG. 6B, lane 1) and the epitope-tagged LGR8 extracted from transfected cells migrated at ~75 KDa when monitored using the M1 antibody after immunoprecipitation with the same antibody (FIG. 6B, lane 4).

Figure 7B:
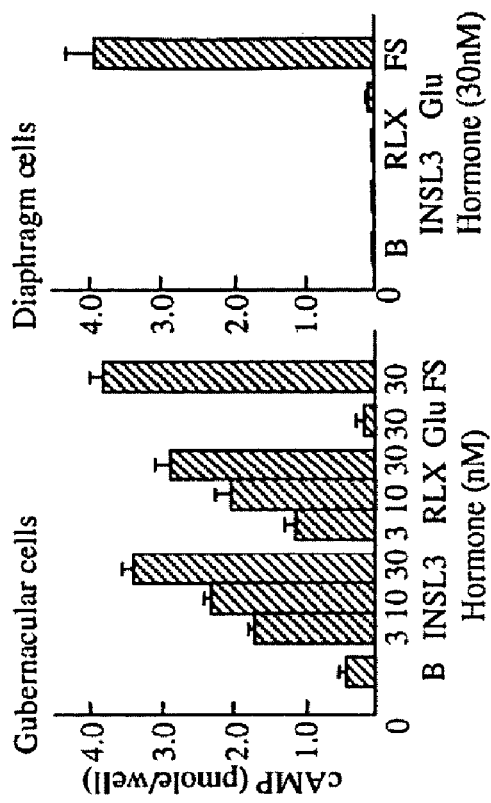
FIG. 7. Expression of LGR8 transcripts in the gubernaculum and INSL3 stimulation of cAMP production and thymidine incorporation by cultured gubernacular cells. A) Northern blot analyses. G: gubernaculum; D: diaphragm; T, testis. B) Stimulation of cAMP production in primary cultures of gubernacular cells treated with rat INSL3, porcine relaxin (RLX) or glucagon (Glu). Some cells were treated with foskolin (FS) served as positive controls whereas diaphragm muscle cells served as negative controls. C) Stimulation of thymidine incorporation by cultured gubernacular cells treated with different hormones for 24 h.
Figure 7C:
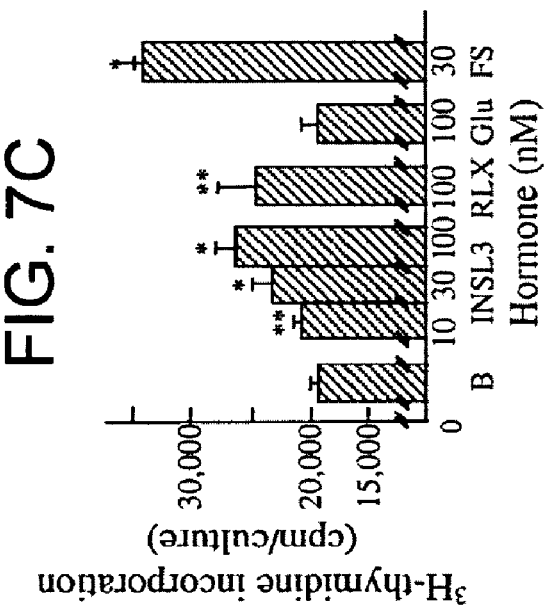
Figure 7A:

Expression of LGR8 in gubernaculum and INSL3 stimulation of gubemacular functions. Northern blotting analyses demonstrated the expression of the LGR8 transcript in the gubernaculum of one-week-old immature rats and testis of adult rats, but not in diaphragm (FIG. 7A). In the gubernaculum, a single transcript of ~2.5 kb was evident whereas an additional transcript of a higher size was found in the testis. In addition, treatment of gubernacular cells with INSL3 led to dose-dependent increases in cAMP production (FIG. 7B) to levels comparable to cells treated with forskolin (FS), a diterpene adenyl cyclase activator. Although glucagon treatment was ineffective, treatment with relaxin also stimulated cAMP production by these cells, consistent with its ability to activate LGR8. For diaphragm cells, none of the hormones tested elicited cAMP production despite the stimulatory effects of forskolin (FIG. 7B). Because an increase in gubernacular cell division is believed to be needed during testis descent, the ability of INSL3 to stimulate thymidine incorporation by cultured gubernacular cells was tested. As shown in FIG. 7C, treatment with INSL3 led to dose-dependent increases in thymidine incorporation by these cells. In addition, treatment with relaxin and forskolin, but not glucagon, was also effective.

The present findings demonstrate that INSL3 is the cognate ligand for LGR8. The observed expression of LGR8 transcripts in the gubernaculum and the INSL3 stimulation of cAMP production by these cells are consistent with the common cryptorchid phenotypes of this ligand-receptor pair in earlier transgenic mouse studies. Although the large 550 kb DNA deletion induced in transgenic mice following random insertional mutagenesis includes genes other than the mouse LGR8 ortholog, present findings of the ligand-receptor relationship for INLS3 and LGR8 supports the hypothesis that deletion of this receptor gene alone is responsible for the cryptorchid phenotype. Despite the bilateral cryptorchidism found in male INSL3 null mice as a result of developmental abnormalities of the gubernaculum, most studies indicated that INSL3 gene mutations are not associated with cryptorchidism in patients. Two putative mutations, R49X and P69L, were identified in the connecting peptide region of the precursor INSL3 protein. Because the frequency of these INSL3 gene mutations is low (1.4%), their potential influence on testis descent-waits further testing. The present identification of LGR8 as the receptor for INSL3 raised the possibility that partial or complete loss-of-function mutations in the LGR8 gene are associated with cryptorchidism, the most frequent congenital abnormalities in humans.

INSL3 specifically activates LGR8, but not LGR7. A total of seven relaxin members are present in the human genome. Relaxin H1 and H2 are clustered together with INSL4 and INSL6 in chromosome 9p23-24 whereas INSL3 is located together with relaxin 3 in 19p13. The present findings provide the basis to test the receptor binding specificity of other relaxin paralogs, thus allowing a better understanding of the evolution and physiology of the relaxin ligand gene family. Based on the divergent receptor specificity of relaxin and INSL3, future chimeric receptor studies on the ligand specificity of LGR7 and LGR8 are also of interest.

During fetal development, the sexual dimorphic position in mammalian gonads is dependent on the differential development of two ligaments. In males, growth of the gubernaculum and regression of the cranial suspensory ligament result in transabdominal descent of the testes. Circulating INSL3 concentrations increase in male rats starting at day 10 of age and continuing until INSL3 concentrations reached adult levels at day 39 after parturition. The testicles are descending into the scrotum during this phase of increasing INSL3 concentrations. INSL3 is expressed in Leydig cells of the fetal and postnatal testis and also in theca and luteal cells of the postnatal ovary, whereas LGR8 is expressed in multiple tissues including testis, brain, kidney, muscle, thyroid, uterus, peripheral blood cells, and bone marrow. In addition to its endocrine role in testis descent mediated by LGR8 in gubernaculum, INSL3 could also have important endocrine or paracrine roles in other tissues. Although defective spermatogenesis found in INSL3 or LGR8 null mice could be the secondary effects of cryptorchidism, Leydig cell-derived INSL3 could play a paracrine role in the testis because LGR8 is also expressed in the testis. In females, INSL3 is expressed in the luteal cells of the ovary through the cycle, and during pregnancy. Because female INSL3 null mice have impaired fertility associated with deregulation of the estrous cycle, the present findings will facilitate understanding of the paracrine role of INSL3 in the ovary in addition to providing understandings on the physiological roles of LGR8 in non-gonadal tissues such as brain, thyroid, and uterus.

All publications and patent applications cited in this specification are herein incorporated by reference as if each individual publication or patent application were specifically and individually indicated to be incorporated by reference. The publications discussed herein are provided solely for their disclosure prior to the filing date of the present application. Nothing herein is to be construed as an admission that the invention is not entitled to antedate such a disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening for biologically active agents that modulate the binding of relaxin to LGR7 the method comprising:
   combining a candidate biologically active agent in vitro with (a) a human LGR7 polypeptide that specifically binds relaxin or (b) a cell comprising a nucleic acid encoding a human LGR7 polypeptide that specifically binds relaxin and comparing in the presence and absence of said agent one or more of: (i) the level of binding of relaxin to LGR7, (ii) the level of binding of relaxin to said agent, and (iii) the level of cAMP production, to thereby identify a biologically active agent that modulates the binding of relaxin to LGR7.

* * * * *